US012573478B2

US 12,573,478 B2

(12) United States Patent
Romanychev et al.

(10) Patent No.: US 12,573,478 B2
(45) Date of Patent: Mar. 10, 2026

(54) SYSTEM AND METHOD FOR COMMUNICATING MEDICAL DATA

(71) Applicant: AR ALLIANCE GROUP, INC., Delray Beach, FL (US)

(72) Inventors: Aleksandr Romanychev, Staten Island, NY (US); Vitaliy Bobkov, Catskill, NY (US)

(73) Assignee: AR ALLIANCE GROUP, INC., Delray Beach, FL (US)

( * ) Notice: Subject to any disclaimer, the term of this patent is extended or adjusted under 35 U.S.C. 154(b) by 314 days.

(21) Appl. No.: 17/545,565

(22) Filed: Dec. 8, 2021

(65) Prior Publication Data

US 2022/0139510 A1     May 5, 2022

Related U.S. Application Data

(63) Continuation-in-part of application No. 17/434,028, filed as application No. PCT/US2020/036256 on Jun.
(Continued)

(51) Int. Cl.
 *G16H 10/60*     (2018.01)
 *G06F 21/32*     (2013.01)
 (Continued)

(52) U.S. Cl.
 CPC ............. *G16H 10/60* (2018.01); *G06F 21/32* (2013.01); *G06F 21/36* (2013.01);
 (Continued)

(58) Field of Classification Search
 CPC ......... G16H 10/60; G06F 21/32; G06F 21/36; G06F 21/6245; H04B 5/72; G06K 7/1417
 (Continued)

(56) References Cited

U.S. PATENT DOCUMENTS 6,988,075 B1    1/2006 Hacker
7,434,724 B2    10/2008 Lane
(Continued)

FOREIGN PATENT DOCUMENTS

WO    WO-2013032869 A1 *   3/2013    ............. G07C 9/257
WO        2014046646 A1     3/2014

OTHER PUBLICATIONS

Kriangsiri Malasri and Lan Wang; Design and Implementation of a Secure Wireless Mote-Based Medical Sensor Network; Published: Aug. 11, 2009 (Year: 2009).*
(Continued)

*Primary Examiner* — Hiep V Nguyen
(74) *Attorney, Agent, or Firm* — Gregory J. Winsky, Esq.; ARCHER & GREINER, P.C.

(57) ABSTRACT

Methods and systems to selectively output access-protected information associated with a code based on biometric data of person from who the code is obtained. An embodiment includes outputting first information upon capture of the code and outputting second information if biometric data obtained from the person matches biometric data associated with the code. The first information may be extracted from the code and the second information may be retrieved from a remote storage device. The biometric data associated with the code may be extracted from the code or retrieved from the remote storage device. The first information may include personal identification information. The second information may include, without limitation, access-protected information, personal medical information, an indication that the person is a member of an at-risk group, or an indication that the person is suspected of involvement in illicit activity. Outputting the first information may be omitted.

2 Claims, 19 Drawing Sheets

Related U.S. Application Data 5, 2020, which is a continuation-in-part of application No. 16/714,356, filed on Dec. 13, 2019.

(60) Provisional application No. 62/857,937, filed on Jun. 6, 2019.

(51) Int. Cl.

| | |
|---|---|
| *G06F 21/36* | (2013.01) |
| *G06F 21/62* | (2013.01) |
| *G06K 7/14* | (2006.01) |
| *H04B 5/20* | (2024.01) |

(52) U.S. Cl.
CPC ....... *G06F 21/6245* (2013.01); *G06K 7/1417* (2013.01); *H04B 5/20* (2024.01)

(58) Field of Classification Search
USPC .............................................................. 705/2
See application file for complete search history.

(56) References Cited

U.S. PATENT DOCUMENTS

| | | | |
|---|---|---|---|
| 7,555,725 | B2 | 6/2009 | Abramson et al. |
| 7,609,155 | B2 | 10/2009 | HinKamp |
| 7,661,146 | B2 | 2/2010 | Karimzadeh et al. |
| 8,050,939 | B2 | 11/2011 | Graves et al. |
| 8,130,407 | B2 | 3/2012 | Nose et al. |
| 8,799,650 | B2 | 8/2014 | Duma |
| 8,960,555 | B1 | 2/2015 | Walton, III |
| 9,224,182 | B2 | 12/2015 | Lacey |
| 9,805,213 | B1 | 10/2017 | Kragh |
| 10,185,834 | B2 | 1/2019 | Adam et al. |
| 11,837,345 | B2 | 12/2023 | Whitaker et al. |
| 2003/0140044 | A1 | 7/2003 | Mok et al. |
| 2006/0274920 | A1 | 12/2006 | Tochikubo et al. |
| 2007/0047770 | A1 | 3/2007 | Swope et al. |
| 2007/0061590 | A1 | 3/2007 | Boye et al. |
| 2009/0259493 | A1 | 10/2009 | Venon et al. |
| 2011/0127325 | A1* | 6/2011 | Hussey .................... G09F 3/005 235/380 |
| 2012/0011585 | A1 | 1/2012 | Otake et al. |
| 2012/0042366 | A1 | 2/2012 | Jin et al. |
| 2012/0280049 | A1 | 11/2012 | Bennett |
| 2013/0054271 | A1 | 2/2013 | Langford |
| 2013/0124523 | A1* | 5/2013 | Rogers .................... G16H 10/60 707/741 |
| 2014/0014720 | A1 | 1/2014 | Sarkis, Jr. et al. |
| 2014/0070012 | A1 | 3/2014 | Hunt et al. |
| 2014/0142963 | A1 | 5/2014 | Hill et al. |
| 2014/0142979 | A1 | 5/2014 | Mitsunaga |
| 2014/0164439 | A1 | 6/2014 | Gale |
| 2014/0263674 | A1 | 9/2014 | Cerveny |
| 2014/0316812 | A1 | 10/2014 | Hathorn et al. |
| 2015/0039338 | A1 | 2/2015 | Tregnagh |
| 2015/0090784 | A1 | 4/2015 | Petalia |
| 2015/0223057 | A1 | 8/2015 | Dellarciprete |
| 2015/0294068 | A1 | 10/2015 | Bartlett et al. |
| 2015/0310173 | A1 | 10/2015 | Coney |
| 2016/0051146 | A1 | 2/2016 | Eaton et al. |
| 2016/0070866 | A1 | 3/2016 | Raju |
| 2016/0092643 | A1 | 3/2016 | Hinkle et al. |
| 2016/0117448 | A1 | 4/2016 | Vande Craen et al. |
| 2016/0224736 | A1 | 8/2016 | Patel |
| 2016/0260002 | A1 | 9/2016 | Hill et al. |
| 2017/0068785 | A1 | 3/2017 | Experton et al. |
| 2017/0169168 | A1 | 6/2017 | Batchelor et al. |
| 2017/0177797 | A1 | 6/2017 | Kurnawan et al. |
| 2017/0186123 | A1 | 6/2017 | Shelton |
| 2017/0339140 | A1 | 11/2017 | Sudduth et al. |
| 2018/0028108 | A1 | 2/2018 | Shluzas et al. |
| 2018/0173864 | A1* | 6/2018 | Boshra .................... G06F 16/58 |
| 2018/0233225 | A1 | 8/2018 | Experton et al. |
| 2018/0349480 | A1 | 12/2018 | Carlisle et al. |
| 2020/0388380 | A1 | 12/2020 | Romanychev et al. |

OTHER PUBLICATIONS

International Search Report and Written Opinion mailed Feb. 22, 2023, issued in connection with corresponding International Application No. PCT/US22/49499 (7 pages total).

Healthcare ID, Retrieved from https://www.slideshare.net/drvit20/health-guard-id; retrieved on Apr. 30, 2019 (9 pages total).

Medical info via QR code, Retrieved from https://www.asiaone.com/health/medical-info-qr-code; retrieved on Apr. 30, 2019 (9 pages total).

PHR Solutions, Retrieved from https://www.phrsolutions.org/phrproducts.html; retrieved on Apr. 30, 2019 (2 pages total).

Zhang et al., "QRM: A QR-code based mHealth information system for patient-centered care", Johns Hopkins University Published 2016—Abstract Only (3 pages total).

Stathis Th Konstantinidis, et al. "A Proposed Framework to Enrich Norwegian EHR System with Health-trusted Information for Patients and Professionals" (2015) Studies in Health Technology and Informatics, 213 , pp. 149-152. (Abstract Only ).

LifeMed ID Healthcare's Identity Solution, Retrieved from https://www.lifemedid.com/; retrieved on May 23, 2019 (8 pages total).

Shih-Syun Lin, et al., "Efficient QR Code Beautification with High Quality Visual Content", IEEE Transactions on Multimedia (vol. 17 , Issue: 9 , Sep. 2015) (22 pages total).

QR Code® Essentials, DENSO ADC, Inventor of the QR Code, Copyright © 2011 DENSO ADC (12 pages total).

International Search Report and Written Opinion mailed Sep. 23, 2020, issued in connection with corresponding International Application No. PCT/US20/36256 (18 pages total).

* cited by examiner 404        104

104

410

500

502 — Collect medical data associated with a patient

504 — Encrypt the collected medical data

506 — Stores the encrypted medical data

508 — Generate medical identifiers

510 — Authorize a user to access the medical data by using the medical identifiers 512 — Display the medical data to the authorized user

550

Collect identification data and medical data associated with an individual — 552

Encrypt the collected data — 554

Stores the encrypted data — 556

Generate an identification code — 558

Enable a personnel to scan the generated identification code — 560

Enable the personnel to validate an identity of the individual — 562

Enable the personnel to access medical data of the individual — 564

Display the medical data to the personnel — 566

SYSTEM AND METHOD FOR COMMUNICATING MEDICAL DATA

CROSS-REFERENCE TO RELATED APPLICATIONS

This application is a continuation in part of U.S. patent application Ser. No. 17/434,028, filed Aug. 26, 2021 which is a § 371 of International Application No. PCT/US2020/036256, filed Jun. 5, 2020, entitled "SYSTEM AND METHOD FOR COMMUNICATING MEDICAL DATA," which is a continuation in part of U.S. patent application Ser. No. 16/714,356, filed Dec. 13, 2019, entitled "SYSTEM AND METHOD FOR COMMUNICATING MEDICAL DATA," which claims the benefit of U.S. Provisional Application Ser. No. 62/857,937, filed Jun. 6, 2019, entitled "SYSTEM AND METHOD FOR COMMUNICATING MEDICAL DATA" all of which are incorporated herein by reference in their entirety.

BACKGROUND

Field

Embodiments of the present invention generally relate to a system and method to communicate medical data and particularly to a system and method for communicating medical data by using medical identifiers.

Description of Related Art

Generally, medical IDs are used to help medical personnel to identify a patient and to obtain the patient's vital medical data quickly and efficiently. The medical personnel can access the medical data of the patient by using the medical IDs within a few seconds. However, there may be some cases in which a user may carry another user's medical ID by mistake or purposefully in order to carry out such as, illegal operations. In another case, a user is travelling to another country with a fake ID. In order to identify a user with a positive or true identity is one of a major task to achieve. However, with the currently available method and systems, a positive identity of a user is not achieved. Furthermore, these medical IDs provide very limited amount of medical data to the medical personnel during emergency conditions or in general pursue different goals and not intended for these purposes at all. For example, a patient may be allergic to certain medications, or certain medications can interfere in the treatment, which might lead to hard complications and may cause even deaths.

Conventionally, a number of systems and devices have been designed to communicate medical data of a patient to medical personnel during emergency conditions like natural disasters, calamity, emergency preparedness, evacuations and other similar situations. The conventional systems use medical data in a printed form. For example, a user fills few details of personal and medical data on a sticker and a paper form provided by, such as, a police department. The sticker is then affixed on a windshield of a vehicle and the paper form is stored in a glove box, or the sticker is affixed on a refrigerator at home and the paper form is stored in a nearby drawer. In case of an emergency situation like natural disasters, calamity, emergency preparedness, evacuations and other similar situations, police personnel can obtain the personal and medical data of the user from the sticker and the paper forms. However, such printed data is not secured and can be accessed by any unauthorized person. And often, it is absolutely outdated. Other conventional systems require a hardware device to be carried by medical personnel to fetch the medical data of the patient. However, these conventional devices are complicated or cannot easily identify the medical data associated with the patient during emergency conditions and are also time-consuming. In addition, these conventional systems require a communication network connection in order to access the medical data associated with the patient, such that the medical data is maintained by a certified Electronic Health Record (EHR) system. In case, the communication network connection is not available, then there is no means to access the medical data, which may lead to a delay in providing a medical treatment to the patient. Also, the medical personnel are required to use a password/Personal Identification Number (PIN) from the patient to access the medical data in an online mode. This further restricts the medical personnel to access the medical data, in case the patient is unable to communicate, or the patient being unconscious, incoherent along with the unavailability of a communication network. Further, these conventional EHR's systems do not generate medical identifiers in order to communicate the medical data to either an emergency first responder or a medical personnel. In addition, the conventional EHR systems do not allow anyone other than the EHR user, such as a patient or a medical personnel, to change and/or update the medical data about the patient especially in case, the medical data is already printed.

There is thus a need for a system and method for communicating medical data to medical personnel during emergency conditions in a more efficient and timely manner.

Also, there is a need for a system and method to communicate medical data of a patient that belongs to an organization such as, United States Army, Police forces, and fire fighters, and so forth to the medical personnel who might save their lives in emergency conditions.

SUMMARY

Embodiments in accordance with the present invention provide a system for validating at least one individual. The system comprising a data collection module configured to collect data, wherein the data comprises identification data and medical data associated with the at least one individual, wherein the identification data comprises at least biometric data, and the medical data comprises a Personal Identifiable Information (PII) data, a Protected Health Information (PHI) data, or a combination thereof. The system further comprising a data transformation module configured to encrypt the collected data of the at least one individual. The system further comprising at least one Electronic Health Record (EHR) database configured to store the encrypted data of the at least one individual. The system further comprising an identifier generation module configured to generate at least one identification code based on the stored encrypted data of the at least one individual, wherein the at least one generated identification code is used for identification of the at least one individual in an offline mode. The system further comprising a scanning module configured to enable at least one personnel to scan the generated at least one identification code of the at least one individual, and a real-time at least one biometric of the at least one individual. The system further comprising a validation module configured to enable the at least one personnel to validate an identity of the at least one individual, wherein the identity of the at least one individual is validated when the at least one scanned real-time biometric of the at least one individual matches with the at least one identification data stored in the at least one of the scanned identification code. The system further comprising a data access module configured to enable the at least one personnel to access the medical data of the at least one individual based on a level of authorization for the at least one personnel defined by the at least one individual when the identity of the individual is valid. The system further comprising a user interface module configured to display the accessed medical data on a user device associated with the at least one personnel.

Embodiments in accordance with the present invention further provide a computer-implemented method for validating an identification data of at least one individual by at least one personnel. The method comprising collecting data, wherein the data comprises identification data and medical data associated with the at least one individual, wherein the identification data comprises at least biometric data, and the medical data comprises a Personal Identifiable Information (PII) data, a Protected Health Information (PHI) data, or a combination thereof; encrypting the collected data of the at least one individual; storing the encrypted data of the at least one individual in at least one Electronic Health Record (EHR) database; generating at least one identification code based on the stored encrypted data of the at least one individual, wherein the at least one generated identification code is used for identification of the at least one user in an offline mode; printing the at least one generated identification code on at least one article; enabling at least one personnel to scan the printed at least one identification code of the at least one individual, and a real-time at least one biometric of the at least one individual; enabling the at least one personnel to validate an identity of the at least one individual, wherein the identity of the at least one individual is validated when the at least one scanned real-time biometric of the at least one user matches with the at least one identification data stored in the at least one of the scanned identification code; enabling the at least one personnel to access to the medical data of the at least one individual based on a level of authorization for the at least one personnel defined by the at least one individual when the identity of the individual is valid; and displaying the accessed medical data on a user device associated with the at least one personnel.

Embodiments in accordance with the present invention provide a system for validating at least one individual. The system comprising a data collection module configured to collect data, wherein the data comprises identification data and medical data associated with the at least one individual, wherein the identification data comprises at least biometric data, and the medical data comprises a Personal Identifiable Information (PII) data, a Protected Health Information (PHI) data, or a combination thereof. The system further comprising a data transformation module configured to encrypt the collected data of the at least one individual. The system further comprising at least one Electronic Health Record (EHR) database configured to store the encrypted data of the at least one individual. The system further comprising an identifier generation module configured to generate at least one identification code based on the stored encrypted data of the at least one individual, wherein the at least one generated identification code is used for identification of the at least one individual in an offline mode. The system further comprising a print module configured to print the at least one generated identification code on at least one article. The system further comprising a scanning module configured to enable at least one personnel to scan the generated at least one printed identification code of the at least one individual, and a real-time at least one biometric of the at least one individual. The system further comprising a validation module configured to enable the at least one personnel to validate an identity of the at least one individual, wherein the identity of the at least one individual is validated when the at least one scanned real-time biometric of the at least one individual matches with the at least one identification data stored in the at least one of the scanned identification code. The system further comprising a data access module configured to enable the at least one personnel to access the medical data of the at least one individual based on a level of authorization for the at least one personnel defined by the at least one individual when the identity of the individual is valid. The system further comprising a user interface module configured to display the accessed medical data on a user device associated with the at least one personnel.

Embodiments in accordance with the present invention provide a health care system for communicating medical data of a patient to at least one user. The health care system disclosed can be used by any government agencies like Police, Firefighters, Army, etc. The system includes a data collection module configured to collect medical data associated with the patient, wherein the medical data comprises biometric data, Personal Identifiable Information (PII) data, a Protected Health Information (PHI) data, or a combination thereof. The system further includes a data transformation module configured to encrypt the medical data of the patient. The system further includes at least one Electronic Health Record (EHR) database configured to store the encrypted medical data of the patient. The system further includes an identifier generation module configured to generate at least one first medical identifier and at least one second medical identifier, wherein the at least one first medical identifier is used to access a first set of the medical data in an offline mode and the at least one second medical identifier is used to access a second set of the medical data in an online mode, wherein the first set of the medical data is categorized into an unprotected PII data and a protected PII data, and the second set of the medical data is categorized into a basic PHI data and an extended PHI data, wherein the unprotected PII data is accessible by the at least one user in an online mode and/or an offline mode, wherein the protected PII data, the basic PHI data, and the extended PHI data are accessible by the at least one user in the online mode only, wherein the extended PHI data is accessible within a medical facility only. The system further includes a data access module configured to authorize the at least one user for providing access to the medical data based on a level of authorization defined by the patient. The system further includes a user interface module configured to display the accessed medical data on the user device.

Embodiments in accordance with the present invention further provide a computer-implemented method for communicating medical data of a patient to at least one user. The method includes collecting medical data associated with the patient, wherein the medical data comprises a Personal Identifiable Information (PII) data, a Protected Health Information (PHI) data, or a combination thereof; encrypting the medical data of the patient; storing the encrypted medical data of the patient in at least one Electronic Health Record (EHR) database; generating at least one first medical identifier and at least one second medical identifier, wherein the at least one first medical identifier is used to access a first set of the medical data in an offline mode and the at least one second medical identifier is used to access a second set of the medical data in an online mode, wherein the first set of the medical data is categorized into an unprotected PII data and a protected PII data, and the second set of the medical data is categorized into a basic PHI data and an extended PHI data, wherein the unprotected PII data is accessible by the at least one user in an online mode and/or an offline mode; wherein the protected PII data, the basic PHI data, and the extended PHI data are accessible by the at least one user in the online mode only; wherein the extended PHI data is accessible within a medical facility only; authorizing the at least one user on the basis of log-in credentials of the at least one user for providing access to the medical data based on a level of authorization defined by the patient; decrypting the accessed medical data; and displaying the decrypted medical data on the user device.

Embodiments in accordance with the present invention provide a health care system for communicating medical data of a patient to at least one user. The system includes a data collection module configured to collect medical data associated with the patient, wherein the medical data comprises a Personal Identifiable Information (PII) data, a Protected Health Information (PHI) data, or a combination thereof. The system further includes a data transformation module configured to encrypt the medical data of the patient. The system further includes at least one Electronic Health Record (EHR) database configured to store the encrypted medical data of the patient. The system further includes an identifier generation module configured to generate at least one first medical identifier and at least one second medical identifier, wherein the at least one first medical identifier is used to access a first set of the medical data in an offline mode and the at least one second medical identifier is used to access a second set of the medical data in an online mode; and embed the unprotected PII data and the second medical identifier in the first medical identifier, such that the second medical identifier is used to access the protected PII data, the basic PHI, the extended PHI data, or a combination thereof; wherein the first set of the medical data is categorized into an unprotected PII data and a protected PII data, and the second set of the medical data is categorized into a basic PHI data and an extended PHI data, wherein the unprotected PII data is accessible by the at least one user in an online mode and/or an offline mode, and the protected PII data, the basic PHI data, and the extended PHI data are accessible by the at least one user in the online mode only, wherein the extended PHI data is accessible within a medical facility only. The system further includes a data access module configured to authorize the at least one user for providing access to the medical data based on a level of authorization defined by the patient. The system further includes a user interface module configured to display the accessed medical data on the user device.

Embodiments of the present invention may provide a number of advantages depending on its particular configuration. First, embodiments of the present application provide a system and a method for communicating medical data of a patient to a user such as a medical personnel during emergency situations such as, but is not limited to, lost seniors with Alzheimer's, accidents, during evacuation, natural disasters, calamity, emergency preparedness, and other emergencies.

Next, embodiments of the present application provide a system and a method that provides medical data to a medical personnel, in case of an available communication network, which may help the user to provide an appropriate and timely medical care to a patient without any delay, and to further prevent minor injuries converting into major ones.

Next, embodiments of the present application may reduce a number of unnecessary tests and procedures of the patient by providing medical data to the user. In addition, embodiments of the present application may identify and share the medical data between various medical institutes, an access to a patient's record even when no communication network connection is available that too in a less amount of time, minimizes time to access medical data of the patient, etc. Also, embodiments of the present application may secure medical data of the patient in an encrypted form, which cannot be accessed by an unauthorized user, and may be accessible through a proprietary medical application with several additional levels of data protection. In addition, for emergency preparedness, the collection and communication of the medical data of a patient to a user may be of prime importance for providing medical treatment to patients in emergency conditions.

Embodiments of the present invention may provide a system and method that acts as an emergency preparedness tool for any disaster management and emergency personnel of local medical facilities as well as State/Federal Disaster and Recovery Agencies during disaster situation, evacuation, natural calamity, earthquake, and other similar situations.

These and other advantages will be apparent from the present application of the embodiments described herein.

The preceding is a simplified summary to provide an understanding of some embodiments of the present invention. This summary is neither an extensive nor exhaustive overview of the present invention and its various embodiments. The summary presents selected concepts of the embodiments of the present invention in a simplified form as an introduction to the more detailed description presented below. As will be appreciated, other embodiments of the present invention are possible utilizing, alone or in combination, one or more of the features set forth above or described in detail below.

BRIEF DESCRIPTION OF THE DRAWINGS

The above and still further features and advantages of embodiments of the present invention will become apparent upon consideration of the following detailed description of embodiments thereof, especially when taken in conjunction with the accompanying drawings, and wherein:

FIG. 5B is a flowchart of a method for communicating data of an individual to a personnel, according to an embodiment of the present invention;

Figure 1:
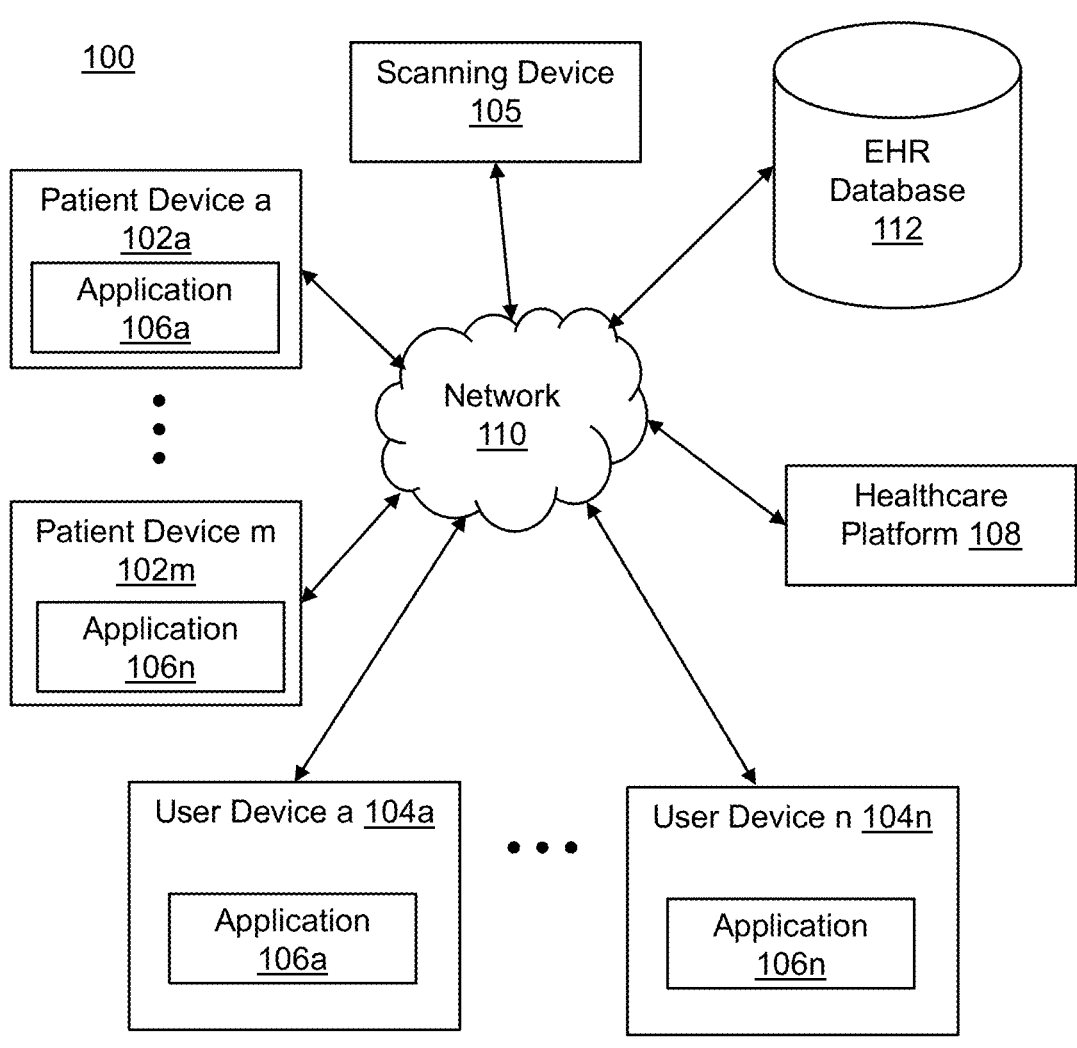
FIG. 1 is a block diagram depicting a health care system for communicating medical data of a patient to a user, according to an embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed.

Human input that consents to the performance of the process or operation is not deemed to be "material".

The terms "determine", "calculate" and "compute," and variations thereof, as used herein, are used interchangeably and include any type of methodology, process, mathematical operation or technique.

The term "individual" and variations thereof, as used herein is defined as a person whose identity is to be validated by an authorized personnel.

The term "patient" and variations thereof, as used herein is defined as a person who is seeking medical treatment from a user. The patient may have a medical ID with an embedded medical identifier, and/or whose identification data for example, fingerprint, face ID, eye scan, Deoxyribonucleic Acid (DNA), and so forth are stored in an Electronic Health Record (EHR) database.

The term "patient representative" and variations thereof, as used herein is defined as a responsible person who is in charge in case when a patient is minor, disabled, and so forth.

The term "firm" and variations thereof, as used herein is defined as an organization who has signed a contract with the health care platform for providing a medical identifier to a patient.

The term "user" and variations thereof, as used herein is defined as a person using a proprietary medical application to access medical data (such as, PII data and PHI data) of a patient, which is stored in the EHR database. The user's credentials and a level of authorization defined by the patient may be used to determine what medical data can be accessed by the user. The user may be a, but is not limited to, an emergency first responder, or an authorized medical personnel. The user may also any authorized personnel such as a law enforcement officer, security officer, etc. working in departments other than healthcare.

The term "First Responder" (FR) and variations thereof, as used herein is defined as a user who is trained to respond or provide basic medical treatment to a patient in case of an emergency situation. Generally, the first responder may be a user with access to a basic medical data of a patient.

The term "Authorized Medical Personnel" (AMP) and variations thereof, as used herein is defined as a user who is authorized to access full medical data of a patient. Generally, the Authorized Medical Personnel may provide medical treatment to a patient in a medical facility, but is not limited to, an emergency room, a hospital, a clinic, or so forth. Also, the medical personnel may only be authorized to access an advanced level of the medical records and charts of a patient stored in the EHR database, when the medical personnel is present within the medical facility.

The term "Medical Emergency Facility" (MEF) and variations thereof, as used herein is defined as a hospital emergency department or any other facility that provides emergency medical services to patients.

The term "Electronic Health Record" (EHR) and variations thereof, as used herein is defined as a certified electronic health record software and/or database that may store a Person's Identification data (PII data), a Person's health records and medical charts (PHI data), billing and accounting data, other data related to patients. The data associated with a patient may be stored as data fields within the EHR database.

The term "unprotected PII data" and variations thereof, as used herein may be defined as a basic PII data fields of a patient that may be available to be read by a commonly used publicly available software application. The unprotected PII data may include, but is not limited to, a name, an emergency contact person name, an emergency contact number, and so forth.

The term "protected PII data" and variations thereof, as used herein may be defined as an extra PII data fields that are being protected to be accessible only by an authorized user. The protected PII data may include, but is not limited to, a Social Security Number (SSN), an address, a unique identifier (e.g., a fingerprint, a DNA, retina, etc.), a face ID, and so forth.

The term "basic PHI data" and variations thereof, as used herein may be defined as a basic PHI data of a patient, which may include, but is not limited to, a blood type, a diabetes type, a DNR, Alzheimer's, common allergies, implants, and so forth. The basic PHI data may be accessed by the users in an online mode as well as in an offline mode.

The term "extended PHI data" and variations thereof, as used herein may be defined as a PHI data that may include full medical records and charts of a patient, which may be based on doctors' visits, hospitalization records, and so forth, which are stored in the EHR database. The extended PHI data may be accessed by only an authorized user in an online mode only and when the user is present in a medical facility.

The term "online mode" and variations thereof, as used herein may be defined as a communication mode that requires a communication network on a user device to access medical data of a patient from the EHR database.

The term "offline mode" and variations thereof, as used herein may be defined as a communication mode that requires no communication network on a user device to access medical data of a patient from the EHR database.

The term "emergency preparedness" and variations thereof, as used herein may be defined as steps taken before, during and after an emergency situation in order to reduce its impact on patients. The emergency situation may include, but not limited to, floods, tornadoes, earthquakes, explosions, fires, lost seniors with Alzheimer's, accidents, evacuations, and so forth.

FIG. 1 is a block diagram depicting a health care system 100 for communicating medical data of a patient to a user, according to an embodiment of the present invention. The user may be a Samaritan, a first responder, or a medical personnel. In another embodiment of the present invention, the system 100 may be used for validating an identity of an individual by an authorized personnel. In an embodiment of the present invention, the medical personnel may be, but not limited to, a general physician, a nurse practitioner, a physician assistant, a surgeon, a medical assistance provider, an emergency rescue team, and so forth. The authorized personnel may include, but not limited to, a law enforcement officer, a security guard, and so forth.

The health care system 100 is capable for communicating medical data of a patient to a user before and/or during a medical treatment for minor and/or major injuries occurred in emergency conditions such as, but not limited to, lost seniors with Alzheimer's, accidents, evacuations, earthquakes, floods, and other emergencies. The minor injury may include, but not restricted to, non-surgical, and/or non-life threatening injuries and the major injury may include, but not limited to, surgical, and/or life-threatening injuries. In another embodiment, the system 100 may be capable for validation of an individual by an authorized personal in places such as, museums, religious places od assembly, recruitment in companies, police stations, high-security laboratories, tourist places, and so forth.

The health care system 100 may include a plurality of patient devices 102a-m (hereinafter referred to as "a patient device 102"). The patient device 102 may be, but is not limited to, a mobile device, a smart phone, a tablet computer, a portable computer, a laptop computer, and so forth. Embodiments are intended to include or otherwise cover any type of a patient device 102, including known, related art, and/or later developed technologies. The patient device 102 may be used by any individual, in an embodiment of the present invention.

Figure 7A:
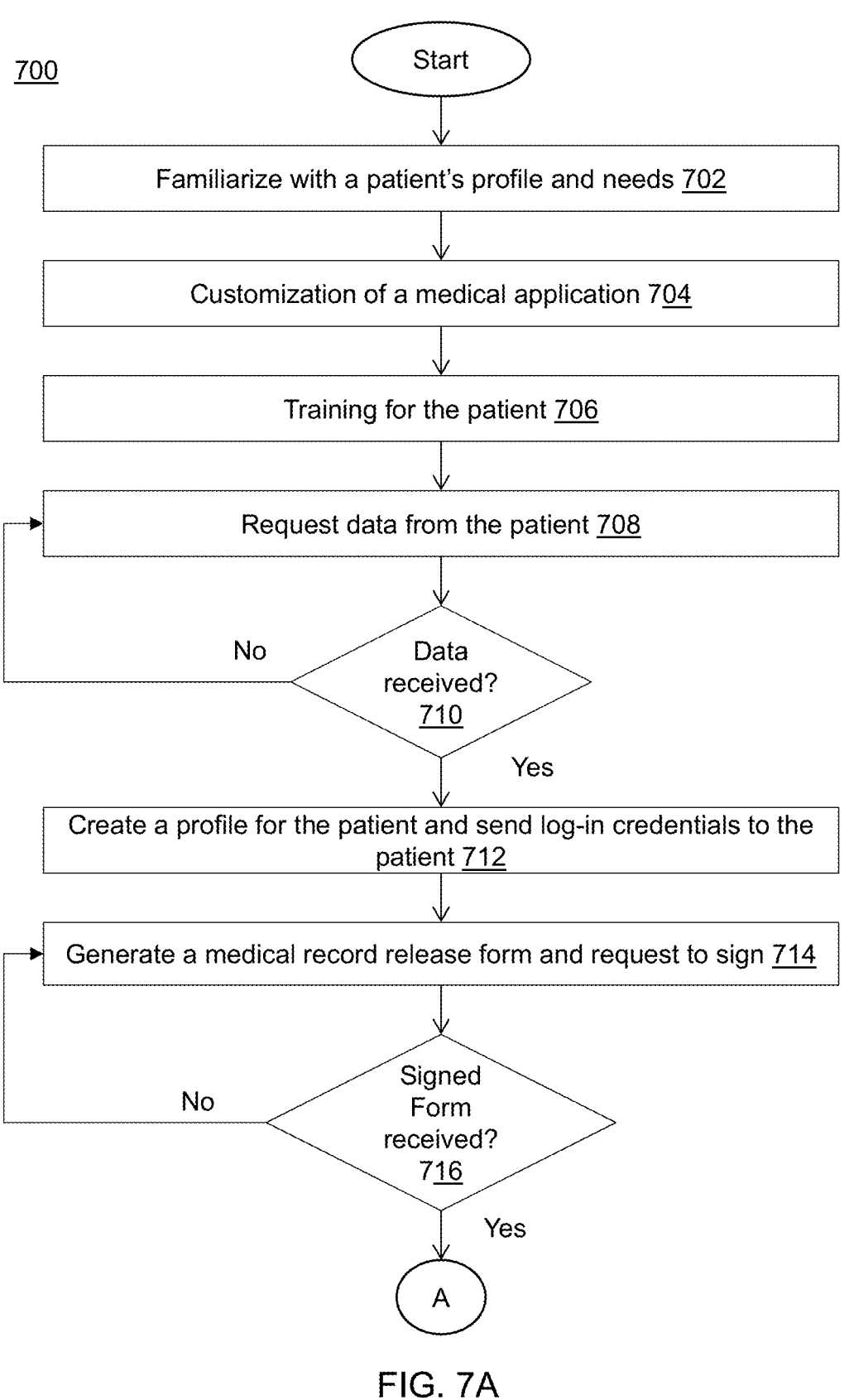
FIGS. 7A and 7B are a flowchart of a method for registering a patient and collecting medical data for record to provide healthcare service to the patient, according to an embodiment of the present invention.
Figure 10:
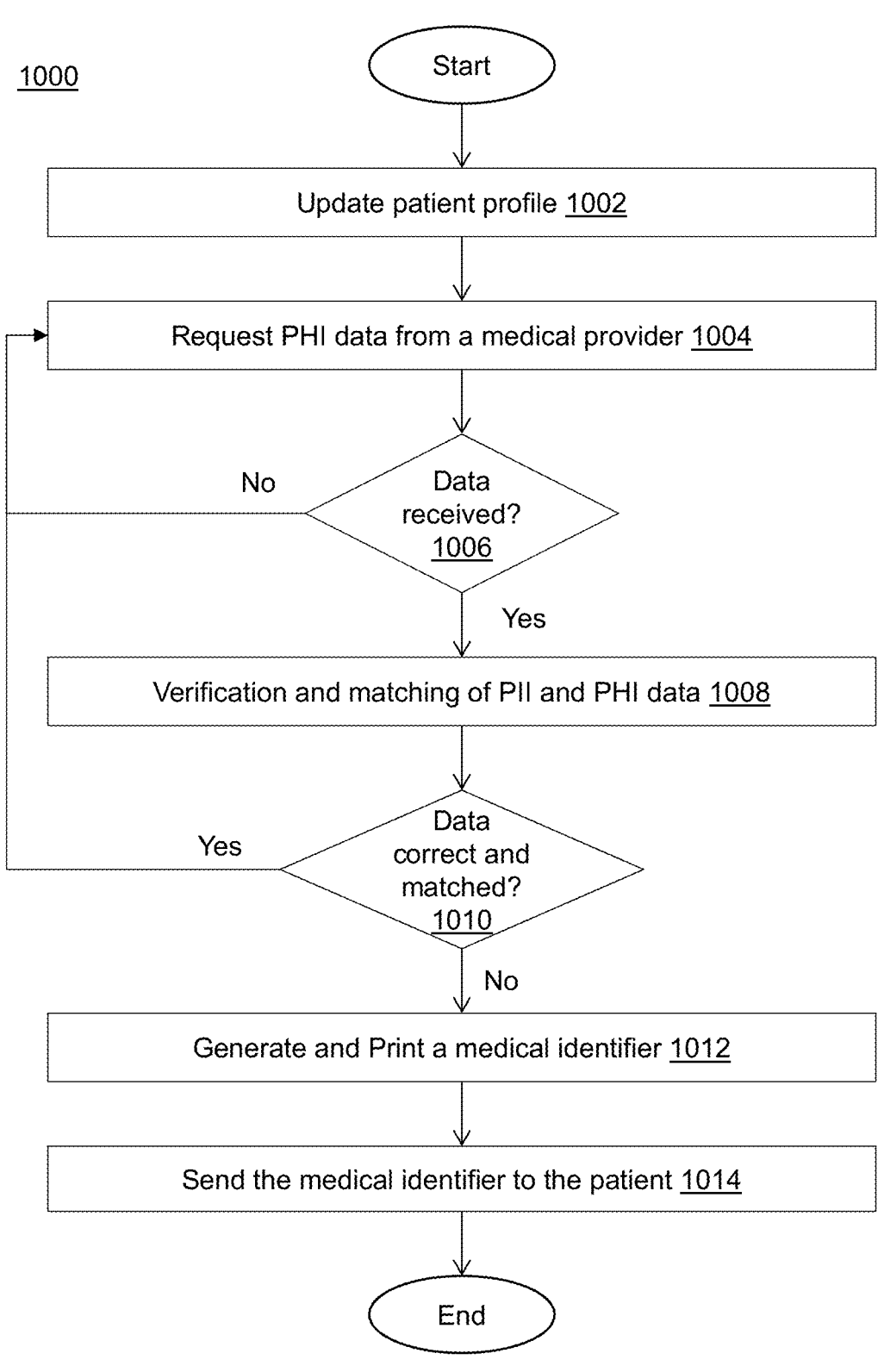
FIG. 10 is a flowchart of a method for updating medical data of a patient, according to an embodiment of the present invention.

Further, the patient device 102 may include one or more software applications such as, but is not restricted to, an ecommerce application, a location-based service application, a navigation application, a camera/imaging application, an Optical Character Recognition (OCR) application, a media player application, a social networking application, and the like. In an embodiment of the present invention, the patient device 102 may include a proprietary healthcare medical application 106a-n (hereinafter referred to as "a medical application 106"). A patient and/or an individual may access the medical application 106 by using log-in credentials, in an embodiment of the present invention. In an embodiment of the present invention, the medical application 106 may be a software application that is registered with a health care platform 108. First, the patient and/or an individual person registers with a service provider of the medical application 106, and a patient and/or an individual person's profile is created, as shown in FIG. 7A. Further, the patient and/or individual person may update the patient profile by providing identification data and/or medical data that may include, Personal Identifiable Information (PII) and/or Protected Health Information (PHI) on the medical application 106, as shown in FIG. 10. In an embodiment of the present invention, the identification data may include, but not limited to, a name, an age, a biometric, and so forth. In an embodiment of the present invention, the Personal Identifiable Information may include any data that may be used to identify a person for example, a patient in a hospital, or a visitor at a museum. The Protected Health Information may be any data such as personal data and/or medical data of the patient, which requires mandating protection and may be accessed only by an authorized user.

Similarly, the health care system 100 may further include a plurality of user devices 104a-104n (hereinafter referred to as "a user device 104"). The user device 104 may be, but is not limited to, a mobile device, a smart phone, a tablet computer, a portable computer, a laptop computer, and so forth. Embodiments are intended to include or otherwise cover any type of user device 104, including known, related art, and/or later developed technologies.

Further, the user device 104 may include one or more software applications such as, but not restricted to, an ecommerce application, a location-based service application, a navigation application, a camera/imaging application, an Optical Character Recognition (OCR) application, a media player application, a social networking application, and the like. In one embodiment of the present invention, the user device 104 may include the proprietary medical application 106. A user may send and/or receive medical data by using the medical application 106, in an embodiment of the present invention. In order to access the medical application 106, the user may log-in within the medical application 106 by using log-in credentials, in an embodiment of the present invention. The user may first register with a service provider of the medical application 106, and then a user profile is created. In an embodiment of the present invention, the user may be a licensed medical practitioner. In another embodiment of the present invention, the user may be an emergency first responder.

Further, the health care system 100 may include a scanning device 105. In an embodiment of the present invention, the scanning device 105 may be any device that is capable of scanning any document (e.g., a text, an image, etc.), and/or physiological or behavioral characteristics of a person, which may include, but not limited to, fingerprints, facial images, iris recognition, retina recognition, voice recognition, and so forth. In an embodiment of the present invention, the scanning device 105 may be any software application installed in the patient device 102, and/or the user device 104, which is publicly available for scanning. The scanning device 105 may be used by any Samaritan to read unprotected PII data of a patient in case of a medical emergency situation. In another embodiment of the present invention, the scanning device 105 may be, but not limited to, a scanner, a barcode reader, a mobile device, a smart phone, a tablet computer, a portable computer, a laptop computer, and so forth. Embodiments are intended to include or otherwise cover any type of scanning device 105, including known, related art, and/or later developed technologies.

Further, the medical application 106 may be managed by a health care platform 108, in an embodiment of the present invention. The working of the health care platform 108 is described in detail in conjunction with FIG. 3. In an embodiment of the present invention, the health care platform 108 may be a software application stored in a server (not shown). In another embodiment of the present invention, the health care platform 108 may be implemented as a hardware, a firmware, a software, or a combination thereof managed by a third-party service provider.

The sharing of the identification data and/or the medical data from the health care platform 108 to the patient device 102, the user device 104 and/or the scanning device 105, or vice versa may be done through a communication network 110. The communication network 110 may include a data network such as, but not restricted to, the Internet, Local Area Network (LAN), Wide Area Network (WAN), Metropolitan Area Network (MAN), etc. In certain embodiments of the present invention, the communication network 110 may include a wireless network, such as, but not restricted to, a cellular network and may employ various technologies including Enhanced Data Rates For Global Evolution (EDGE), General Packet Radio Service (GPRS), Global System For Mobile Communications (GSM), Internet Protocol Multimedia Subsystem (IMS), Universal Mobile Telecommunications System (UMTS) etc. In some embodiments of the present invention, the communication network 110 may include or otherwise cover networks or sub-networks, each of which may include, for example, a wired or wireless data pathway. The communication network 110 may include a circuit-switched voice network, a packet-switched data network, or any other network capable for carrying electronic communications. For example, the communication network 110 may include networks based on the Internet Protocol (IP) or Asynchronous Transfer Mode (ATM), and may support voice usage, for example, VoIP, Voice-over-ATM, or other comparable protocols used for voice data communications.

Examples of the communication network 110 may further include, but are not limited to, a Personal Area Network (PAN), a Storage Area Network (SAN), a Home Area Network (HAN), a Campus Area Network (CAN), a Local Area Network (LAN), a Wide Area Network (WAN), a Metropolitan Area Network (MAN), a Virtual Private Network (VPN), an Enterprise Private Network (EPN), the Internet, a Global Area Network (GAN), and so forth. Embodiments are intended to include or otherwise cover any type of communication network, including known, related art, and/or later developed technologies to connect the components of the health care system 100 with each other.

Further, the identification data and/or the medical data shared by the patient and/or the user may be stored in a database. In an embodiment of the present invention, the database may be an Electronic Health Record (EHR) database 111. In an embodiment of the present invention, the Personal Identifiable Information (PII) data may be stored in the EHR database 111. In another embodiment of the present invention, the Protected Health Information (PHI) data may be stored in the EHR database 111. The EHR database 111 may electronically store the medical data of patients in a structured digital format. The structured digital format may enable the users to easily search for medical data associated with a patient, which may aid patient care. The stored medical data may then be accessed by various healthcare user when required in medical emergency conditions. The EHR database 111 may store the medical data in compliance with Health Insurance Portability and Accountability Act (HIPAA). The EHR database 111 may be a certified database when it meets the standards and regulatory requirements defined by the federal government.

Figure 2:
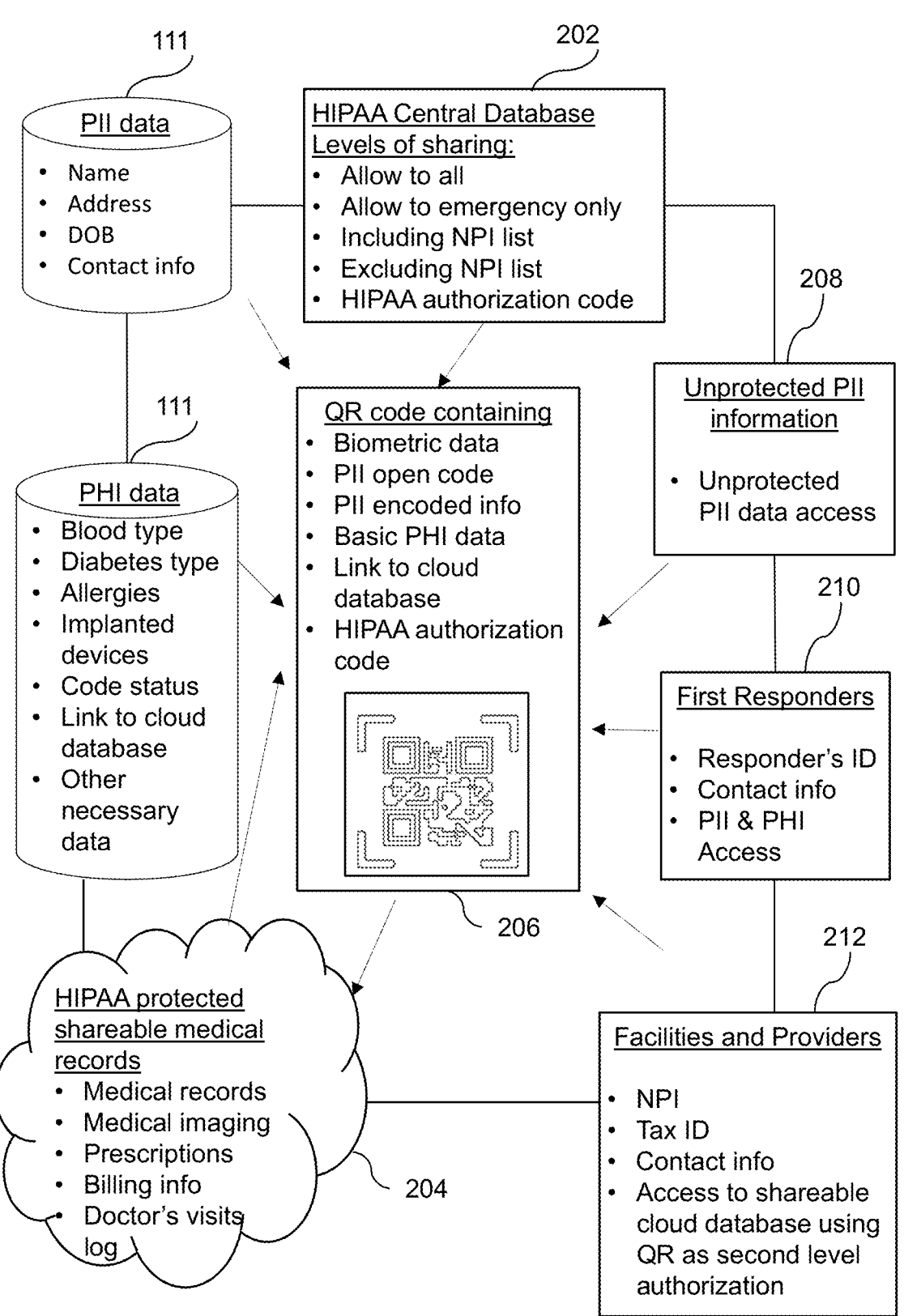
FIG. 2 is a block diagram depicting medical data stored in different components of the health care system, according to an embodiment of the present invention.

FIG. 2 is a block diagram depicting medical data stored in different components of the health care system 100, according to an embodiment of the present invention.

The identification data may include, but not limited to, biometric data of an individual. The Personal Identifiable Information (PII) data may be stored in the EHR database 111, such that the PII data may include, but not limited to, a name, an address, a date of birth, a contact information, a social security number, an employee ID, types of identification allergies, types of implants, a person being Alzheimer's, common medication, any other common and rarely changeable health information specifics of an industry (e.g., military, police force, etc.), and so forth. Further, the Protected Health Information (PHI) data may include, but not limited to, a blood type, a diabetes type, allergies, implanted devices, a code status, a link to a cloud database, a common organ donor, an Alzheimer's type of specific data based on a user's requirement and specifics of an industry (e.g., police force, military, etc.), and so forth. The PHI data may be stored in the EHR database 111, in an embodiment of the present invention. In an embodiment of the present invention, each of the medical data provided by the patient may be stored as a data form in the database such as, the EHR database 111.

A cloud database that is linked to the Protected Health Information (PHI) may store other necessary information like medications and/or surgeries. Also, as every agency, hospital or any other medical facility may request some specific information about the patient, the PHI data may be accustomed accordingly.

The Personal Identifiable Information (PII) stored in the EHR database 111 may also comprise other necessary information like name of a government organization or a corporate with which a user is associated, rank of the user, user official identification number, etc.

In addition, the patient and/or an individual may define a level of sharing 202 for each data form stored in the EHR database 111, in an embodiment of the present invention. The level of sharing may include, but not limited to, allow to all, allow to emergency only, including National Provider Identifier (NPI) list, excluding NPI list, an authorization code in compliance with Health Insurance Portability and Accountability Act (HIPAA), which may grant access to a user for a specific patient only, and so forth. In an embodiment of the present invention, the level of sharing 202 may be stored in the database such as, the EHR database 111, or any other database with a patient medical code to identify medical data associated with the patient. Further, the medical data provided by the patient may be filtered, by the health care platform 108, as a protected shareable medical data 204, and an unprotected medical data 208. The protected medical data 204 may include the extended PHI data such as, but not limited to, medical records, a medical imaging, prescriptions, billing information, a log of visits to one or more medical personnel, and so forth. The unprotected medical data may be, but not limited to, the unprotected PII data 208 that may include, but not limited to, a name, an emergency contact person name, an emergency contact number, and so forth.

Further, the medical data and their level of sharing, defined by the patient may be embedded in a medical identifier 206. In another embodiment of the present invention, the identification data may be embedded in an identification code 206. In an embodiment of the present invention, the medical identifier 206 may be, but not limited to, a Quick Response (QR) code, a Bar code, a unique identifier, such as a biometric, and so forth. In an embodiment of the present invention, the medical identifier 206 may include data such as, but not limited to, a PII open code, a PII encoded code, a second medical identifier (e.g., a URL to the EHR database 111 that stores the protected medical data 204), an authorization code, a patient code, and so forth. In case of an event, such as, an accident, a first emergency responder 210 may access a set of the medical data associated with a patient by scanning a medical identifier associated with the patient through a registered software application such as the medical application 106, even in an offline mode. The set of medical data accessed by the first responder may include, but not limited to, the unprotected PII data, protected PII data, and the basic PHI data. In an embodiment of the present invention, the first responder 210 may access the unprotected PII data even in an offline mode. In another embodiment of the present invention, the first responder 210 may access the protected PII data and the basic PHI data of the patient, only in an online mode, based on the authorization of the first responder's ID, a contact information, etc.

Further, after authorization of the first responder 210, the health care system 100 may provide facilities 212 to the user, which may include data such as, but not limited to, a NPI, a tax ID, a contact information, an access to a shareable database (e.g., the EHR database 111) comprising the medical data of the patient. In an embodiment of the present invention, the first responder 210 may access the medical data by using the first medical identifier and log-in credentials of the patient as well as the responder's, only in an online mode. The accessed medical data by the first responder 210 may assist in providing a best medical aid to the patient and may avoid possible complications and risks.

Figure 3:
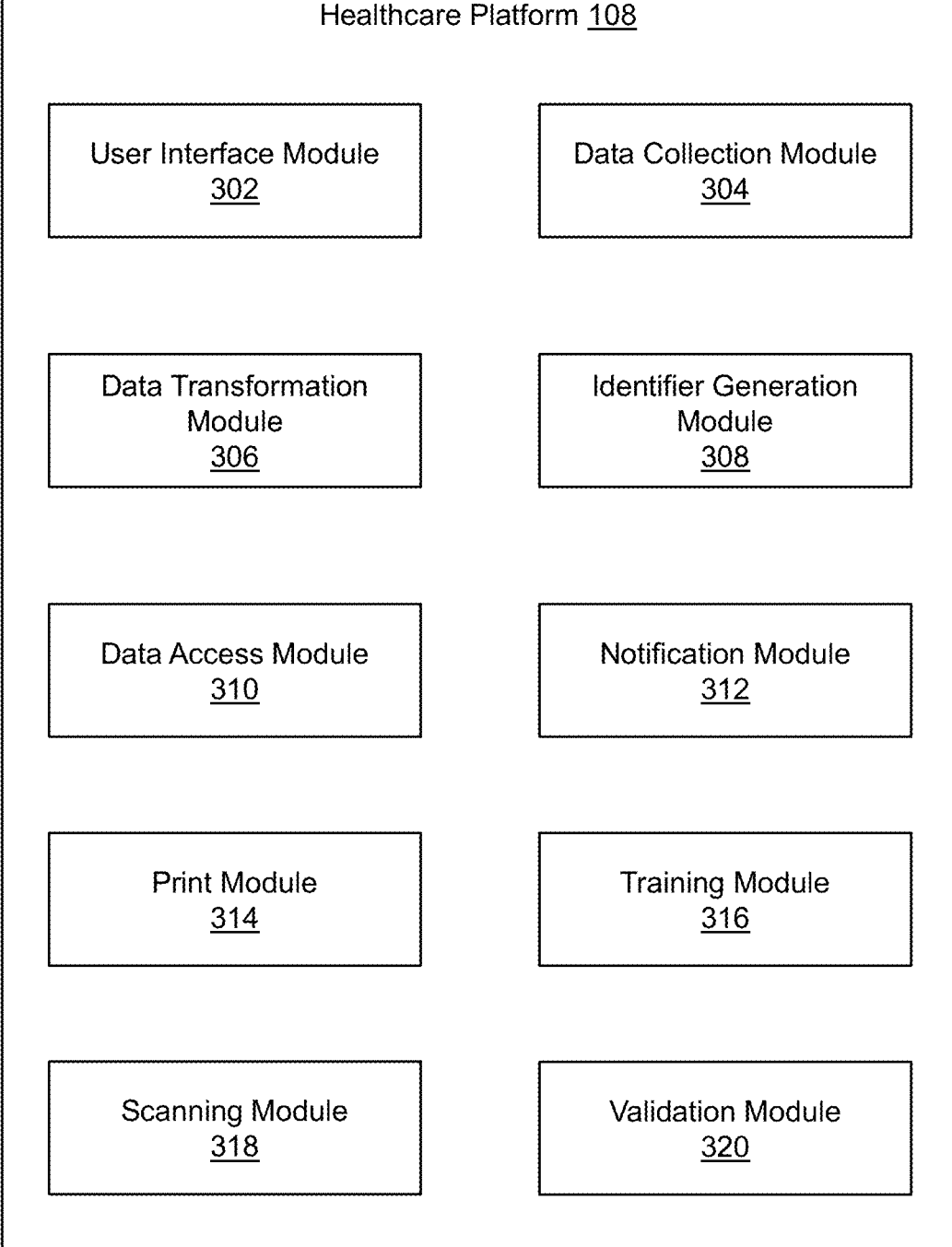
FIG. 3 is a block diagram depicting components of a health care platform, according to an embodiment of the present invention.

FIG. 3 is a block diagram depicting components of the health care platform 108 of the health care system 100, according to an embodiment of the present invention. The health care platform 108 may include, but not limited to, a user interface module 302, a data collection module 304, a data transformation module 306, an identifier generation module 308, a data access module 310, a notification module 312, and a print module 314.

The user interface module 302 may be configured to provide a user interface of the medical application 106 on the patient device 102 and/or the user device 104. First, the patient and/or an individual may install the medical application 106 in the patient device 102, in an online mode. The health care platform 108 may then create an account on the medical application 106 for the patient to avail medical services/treatment during and/or after emergency situations, such as, but not limited to, an accident, evacuation, etc. In another embodiment of the present invention, the health care platform 108 may create an account on the medical application 106 for the individual for identification purposes. In an embodiment of the present invention, the user interface module 302 may function in conjunction with the data collection module 304 in order to collect information from the patient and/or an individual. In an embodiment of the present invention, the information may include, but not limited to, a name, an age, a date of birth, a residential address, an office address, medical data, medical reports, prescriptions, a blood type, an emergency note, an emergency contact, biometric data, and so forth. In another embodiment of the present invention, the patient and/or an individual may define a level of sharing of the medical data such as, whether the patient and/or an individual desires to disclose complete or limited medical data to a user, a duration (e.g., all past, present and future period, from the date signed until following event, etc.) for which the user may access the medical data, whether the medical data to be disclosed with any user requesting the medical data during a treatment, a current user under Business Associate Agreements (BAA) only, which is a type of legal contract that must be signed between parties that use, transmit, receive or exchange the medical data, for example, between a patient and a user, defined user only, any user except a defined user, an emergency only, and so forth. In an embodiment of the present invention, the level of sharing of the medical data may be defined in compliance with HIPAA.

The user interface module 302 may further be configured to provide a user interface of the medical application 106 on the user device 104 to the medical personnel to receive medical data associated with a patient for providing medical assistance. The user may register with the health care platform 108 and the health care platform 108 may then create an account on the medical application 106. The health care platform 108 may provide log-in credentials to the user, in an embodiment of the present invention. The user may provide information, such as, but not limited to, a name, a medical license number, a contact information, specialization, etc. In an embodiment of the present invention, the user interface module 302 may function with the data collection module 304 to collect the data of the user.

Further, the user interface module 302 may be configured to display a log-in user interface of the medical application 106 on the user device 104 in an online mode. The user may log-in the medical application 106 by using the log-in credentials, such as, but not limited to, a sign-in ID and a password, and/or a unique identifier, for example, a fingerprint, a face recognition, retina, etc. Embodiments of the present invention are intended to include or otherwise cover any type of data, including known, related art, and/or later developed technologies to securely log-in into the medical application 106.

Furthermore, the user interface module 302 may be configured to customize the medical application 106 based on a type of user, in an embodiment of the present invention. In an exemplary embodiment, the user interface module 302 may customize the medical application 106 for a patient, in which the patient may locate nearby hospitals, medical records, medical personnel contact information, and so forth. In addition, the user interface module 302 may customize the medical application 106 for a medical personnel, in which the medical personnel may retrieve medical records of associated patients.

The data collection module 304 may be configured to generate a medical records release form to be signed by the patient, in an embodiment of the present invention. The medical records release form may be a form that provides a written authorization for the users to release medical data to the patient as well as a representative of the patient. The data collection module 304 may further be configured to share the medical records release form with a patient. The patient may then share the signed medical records release form with the health care platform 108.

The data collection module 304 may further be configured to verify the data received from the patient and/or the medical personnel, in an embodiment of the present invention. In case, if the medical data is not verified, then the data collection module 304 in communication with the notification module 312 may provide an alert to the patient and/or the medical personnel to provide correct medical data.

Further, the data collection module 304 may be configured to collect the identification data of the individual, in an embodiment of the present invention. The identification data may include, but not limited to, biometric data of the individual along with the medical data.

Furthermore, the data collection module 304 may be configured to update the data received from the patient, individual, and/or the medical personnel, in an embodiment of the present invention. The data may be updated periodically, such as, but not limited to, weekly, bi-weekly, monthly, every four days, and so forth.

The data collection module 304 may be configured to store the verified data collected from the patient and/or the individual, or user in a database, such as, the EHR database 111, in an embodiment of the present invention.

Further, the data collection module 304 may be configured to categorize the medical data based on factors, such as, but not limited to, personal data, medical data, level of sharing defined by the patient and/or HIPAA rules and regulations, and so forth. In an embodiment of the present invention, the medical data may be divided into two categories, a Personal Identifiable Information (PII), and a Protected Health Information (PHI). In an embodiment of the present invention, the PII data may include, but not limited to, a name, an address, a date of birth, a contact information, social security number, employee ID, types of identification allergies, types of implants, person being Alzheimer's, common medication, any other common and rarely changeable health information specifics of an industry (e.g., military, police force, etc.), and so forth. The PII data may further be categorized into an unprotected PII data and a protected PII data. The unprotected PII data may include, a name, a contact person's information, and so forth, which may be accessed by any user even in an offline mode. The protected PII data such as, but not limited to, social security number, employee ID, types of identification allergies, types of implants, person being Alzheimer's, common medication, any other common and rarely changeable health information specifics of an industry etc. may be accessed by an authorized user and in either an online mode or an offline mode.

Further, the PHI data may include, but not limited to, a blood type, a diabetes type, allergies, implanted devices, a medical code status, a common organ donor, Alzheimer's type of specific data based on a user's requirement and specifics of an industry, and so forth. The PHI data may further be categorized into a basic PHI data and an extended PHI data. The basic PHI data may include, but is not limited to, a blood type, a diabetes type, a DNR, Alzheimer's, common allergies, implants, and so forth which may be accessed by an authorized user and in an online mode and/or an offline mode. On the other hand, the extended PHI data may include full medical records and charts of a patient, which may be based on doctors' visits, hospitalization records, and so forth, and may be accessed by an authorized user and in an online mode only.

In addition, the data collection module 304 may further be configured to enable the patient and/or the individual, and/or the user to update the medical data periodically, in an embodiment of the present invention.

The data transformation module 306 may be configured to transform the identification data, medical data into a secured format, in an embodiment of the present invention. The data transformation module 306 may encrypt the medical data in order to eliminate unauthorized access to the identification data, medical data. Encryption is a technique that renders the data into an unreadable form, which may be accessed only by an authorized user that holds a key and/or password to render the data into a readable form. In an embodiment of the present invention, the data transformation module 306 may encrypt the identification data, basic PHI data and/or the extended PHI data. In another embodiment of the present invention, the data transformation module 306 may encrypt the protected PII data. In yet another embodiment of the present invention, the data transformation module 306 may encrypt the protected PII data, the basic PHI data, and the extended PHI data.

The data transformation module 306 may further be configured to decode the encrypted identification data, and medical data. In an embodiment of the present invention, the data transformation module 306 may decode the encrypted medical data when an authorized user accesses the encrypted identification data, and the medical data. The data transformation module 306 may function in conjunction with the data access module 310 to decode the encrypted identification data, and the medical data. In an exemplary scenario, when a user is authorized by the data access module 310 to access the medical data, then the data transformation module 306 may decode the encrypted identification data, and the medical data required by the user.

The identifier generation module 308 may be configured to generate at least one identification code based on the stored encrypted data of the individual. The identification code may be for example, but not limited to, a Quick Response (QR) code. The generated identification code may be used for identification of the individual in an offline mode. Further, the identifier generation module 308 may be configured to embed the identification data into the identification code.

The identifier generation module 308 may be configured to generate one or more medical identifiers associated with the patient. The identifier generation module 308 may be configured to generate a first medical identifier that may be used to access a first set of the medical data. The first set of the medical data may be accessed by a user even in an offline mode. In an embodiment of the present invention, the first medical identifier may be, but not limited to, a Quick Response (QR) code, a bar code, and so forth. In an exemplary scenario, when a patient meets with an accident, an emergency first responder may help the patient to get first aid by scanning the first medical identifier, i.e., QR code. The first medical identifier may be scanned by any Optical Character Recognition (OCR) device, such as, but not limited to, a scanner, a smart phone, a mobile device, and so forth. In case, the user scans the first medical identifier by any software application or a scanning device, then the user may only access an unprotected PII data associated with the patient even in an offline mode. In case, the user is authorized and is in an offline mode, then the authorized user may access the unprotected PII data and a basic PHI data of the patient by scanning the first medical identifier using the proprietary medical application 106. In case, the user is authorized and is in an online mode, then the authorized user may access the unprotected PII data, the protected PII data, and the basic PHI data of the patient by scanning the first medical identifier using the proprietary medical application 106. In an embodiment of the present invention, the identifier generation module 308 may be configured to embed the first medical identifier into the identification code.

The identifier generation module 308 may further be configured to generate a second medical identifier that may be used to access a second set of the medical data in an online mode only. The second medical identifier may be, but not limited to, a Uniform Resource Locator (URL). The second medical identifier may be used as a web link to access the medical data stored in the EHR database 111. In an embodiment of the present invention, the second medical identifier may be used by a user such as, an authorized medical personnel, to access the extended PHI data that may be used to provide medical aid to the patient only in an online mode only. In an embodiment of the present invention, the identifier generation module 308 may be configured to embed the second medical identifier into the identification code.

The identifier generation module 308 may be configured to generate a new medical identifier, in case, updated medical data is received by the data collection module 304.

The identifier generation module 308 may further be configured to adjust the size of the first medical identifier based on the requirement of the patient. In an embodiment of the present invention, the size of the first medical identifier may be, but not limited to, 1.6 inch by 1.6 inch. The bigger the size of the first medical identifier, the more medical data it may store. In an exemplary scenario, a first medical identifier of size 0.75 inch by 0.75 inch may store 234 characters, a first medical identifier of size 0.9 inch by 0.9 inch may store 279 characters, and a first medical identifier of size 1.2 inch by 1.2 inch may store 587 characters. In an embodiment of the present invention, the generated first medical identifier may then be shared with the patient, which may be printed on an article, for example, but not limited to, a wristband, a dog tag, a driving license, a passport, a car windshield, a credit card, a ID card, a wearable jewelry, a refrigerator magnet, a chain, a mobile phone, a helmet, and so forth. Embodiments of the present invention may cover or intend to include any type of an article that the patient carries at most/every time.

Further, the identifier generation module 308 may be configured to embed the medical data into the medical identifiers. In an embodiment of the present invention, the identifier generation module 308 may be configured to embed the PII data into the first medical identifier. In an embodiment of the present invention, the identifier generation module 308 may embed the unprotected PII data into the first medical identifier in a non-encrypted format, which may be read by any scanning application and/or device, such as, but not limited to, a scanner. In another embodiment of the present invention, the protected medical data, such as, but not limited to, the protected PII data, the basic PHI data, or a combination thereof may be embedded in the first medical identifier in an encrypted format, which may be decoded by using the medical application 106 of an authorized user device 104.

The identifier generation module 308 may further be configured to embed a second medical identifier such as, a URL into the first medical identifier, which may be used to access the extended PHI data of the patient through the medical application 106 of the user device 104.

The print module 314 may be configured to print the identification code, in an embodiment of the present invention. The identification code may be printed on an article such as, but not limited to, a label, a passport, a wristband, ID cards, wearable articles, and so forth. Further, the print module 314 may be configured to print the first medical identifier. In an embodiment of the present invention, the print module 314 may be configured to print the first medical identifier on an article.

The scanning module 318 may be configured to scan the identification code printed on the article. In an embodiment of the present invention, the scanning module 318 may be configured to scan biometrics of the individual in real-time.

In an embodiment, a medical identifier is provided in a static/physical form (e.g., a sticker, printing on wearables jewelry, driver's licenses, etc.). Alternatively, or additionally, a medical identifier is provided in a dynamic form (e.g., electronic/computer storable/readable form). A dynamic medical identifier may be downloaded to a smart user device (e.g., a mobile telephone and/or a wearable device), such as user device 104 in FIGS. 1 and 4A-4G. A dynamic medical identifier may be useful to permit updating (e.g., over a wireless network). A static medical identifier may be useful in a situation where a dynamic medical identifier is inaccessible (e.g., in a situation where the client is physically and/or mentally unable to operate/unlock the device, and/or where the device is inaccessible, damaged, or without electrical power).

The data access module 310 may be configured to enable the personnel to access the medical data of the individual based on a level of authorization for the personnel defined by the individual. In an embodiment of the present invention, the data access module 310 may be configured to enable the personnel such as, but not limited to, a medical personnel during a medical emergency, to access the medical data of the individual only when an identity of the individual is validated by the validation module 320. In an embodiment of the present invention, the medical data may be accessed from the EHR database 111. Further, the data access module 310 may be configured to enable the personnel to access the medical data of the individual in an offline mode. Further, the data access module 310 may be configured to provide access to the identification data to the personnel in the offline mode, when the generated identification code is scanned by the medical application 106.

The data access module 310 may be configured to authorize a patient and/or a user to access the medical data stored in the EHR database 111. In an embodiment of the present invention, the data access module 310 may be configured to identify a patient whose medical data is stored in the EHR database 111, based on log-in credentials such as, a user ID and a password, a unique identifier or biometric, for example, a fingerprint, a face ID, and so forth. In another embodiment of the present invention, the data access module 310 may be configured to identify and/or authorize a user based on log-in credentials such as, a user ID and a password, a unique identifier, for example, a fingerprint, a face ID, and so forth to access the medical data associated with a patient.

In case, the user is, for example, a Samaritan, then the user scans the first medical identifier either by any scanning application or a scanning device, and may access the unprotected PII data associated with the patient in an offline mode.

In case, the user is a first responder and scans the first medical identifier by using the medical application 106, then the user is authorized based on the log-in credentials. In case, the log-in credentials of the user matches with the stored credentials of the user, then the data access module 310 may authorize the user and a permission is granted to the user to access the unprotected PII data, the protected PII data, the basic PHI data, or a combination thereof, in the online mode and/or offline mode.

In case, the user is a medical personnel, and scans the first medical identifier by using the medical application 106, then the user is authorized based on the log-in credentials. In case, the log-in credentials matches with the stored credentials of the user, then the data access module 310 may authorize the user and a permission is granted to the user to access the unprotected PII data, the protected PII data, the basic PHI data, or a combination thereof in the offline mode and/or online mode, and to access the extended PHI data, in the online mode only. In an embodiment of the present invention, in an online mode, the authorized medical personnel may click on the URL to access the extended PHI data of the patient stored in the EHR database 111. In another embodiment of the present invention, the authorized medical personnel may click on the URL, and also scan a unique identifier, such as a biometric of the patient using the medical application 106 to access the extended PHI data associated with the patient. In yet another embodiment of the present invention, the authorized medical personnel may scan the unique identifier of the patient using the medical application 106, which may act as a URL to access the extended PHI data associated with the patient. In an embodiment of the present invention, the authorized medical personnel may access the extended PHI data associated with a patient in an online mode only and when the authorized medical personnel is present within the vicinity of the medical facility such as, an emergency room, a hospital, a clinic, and so forth.

Further, the data access module 310 may be configured to enable the user to download and/or save a copy of the medical data on the user device 104, in an online mode. The user may download the medical data of the patient, which may further be consulted during the treatment of the patient. In an offline mode, the user may consult the downloaded/saved medical data during the treatment. In addition, the data access module 310 may be configured to download the medical data in a predetermined order. In an embodiment of the present invention, the predetermined order may be defined by the service provider of the health care platform 108, or is based on laws in compliance with HIPAA. The medical data stored in the database in the data form may be downloaded as a data string in the medical personnel device 104.

Further, the data access module 310 may be configured to automatically terminate an electronic session or logs-off the user from the medical application 106 on the user device 104 after a predetermined time of inactivity. The data access module 310 may provide the user to access the medical data of a patient for a specific time duration, for example, during a treatment of the patient. Further, the data access module 310 may be configured to automatically logs-off the user from the medical application 106 in compliance with HIPAA laws and/or due to inactivity on the medical application 106 for a preset period of time and therefore terminate an electronic session between the user device 104 and the database, such as, the EHR database 111.

Also, the data access module 310 may be configured to enable the patient and/or user to locate a nearest hospital in a defined area such as, within five miles, or 10 miles, etc. In order to find a nearest hospital, a Global Positioning System (GPS) of the patient device 102 and/or the user device 104 may be turned on, in an embodiment of the present invention. In addition, the data access module 310 may be configured to enable the patient and/or user to find an address on the medical application 106. In an embodiment of the present invention, the data access module 310 may be configured to direct the patient and/or user on a navigation application of the patient device 102 and/or the user device 104 in order to find an address.

Further, the notification module 312 may be configured to generate a notification. In an embodiment of the present invention, the notification module 312 may generate a notification when the medical data is accessed by a user. The notification may include, but not limited to, a name of hospital, a contact details of the hospital, a name of the user, a location of the patient, and so forth. The notification module 312 may further be configured to transmit the notification to an emergency contact whose information is provided by the patient. In an embodiment of the present invention, the notification may be transmitted by, but not limited to, a text message, an email, a voice call, and so forth.

The training module 316 may be configured to enable an employee of a firm that provides the medical identifier to the patients, to provide trainings on the usage of the medical application 106, in an embodiment of the present invention. In another embodiment of the present invention, the training module 316 may be configured to provide trainings to the medical personnel to scan the medical identifiers and retrieve the medical data associated with a patient.

The validation module 320 may be configured to enable the personnel to validate an identity of the individual. The validation module 320 may be configured to enable the personnel to identify a positive identity of an individual by scanning biometric of the individual in real-time and the identification code printed on an article associated with the individual. In an embodiment of the present invention, the scanning of the biometric of the individual in real-time and the identification code may be done by using the medical application 106. The validation module 320 may further be configured to compare the scanned real-time biometric of the individual with the biometric data embedded in the identification code associated with the individual. In case, the validation module 320 determines that the scanned real-time biometric of the individual matches with the biometric data embedded in the identification code associated with the individual, then the validation module 320 may be configured to validate the identity of the individual as a positive identity. On the other hand, in case, the validation module 320 determines that the scanned real-time biometric of the individual does not match with the biometric data embedded in the identification code associated with the individual, then the validation module 320 may invalidate the identity of the individual as a negative identity. Further, the validation module 320 may be configured to transmit the identified identity of the individual.

The notification module 312 may be then configured to notify about the identity of the individual to the personnel.

Figure 4A:
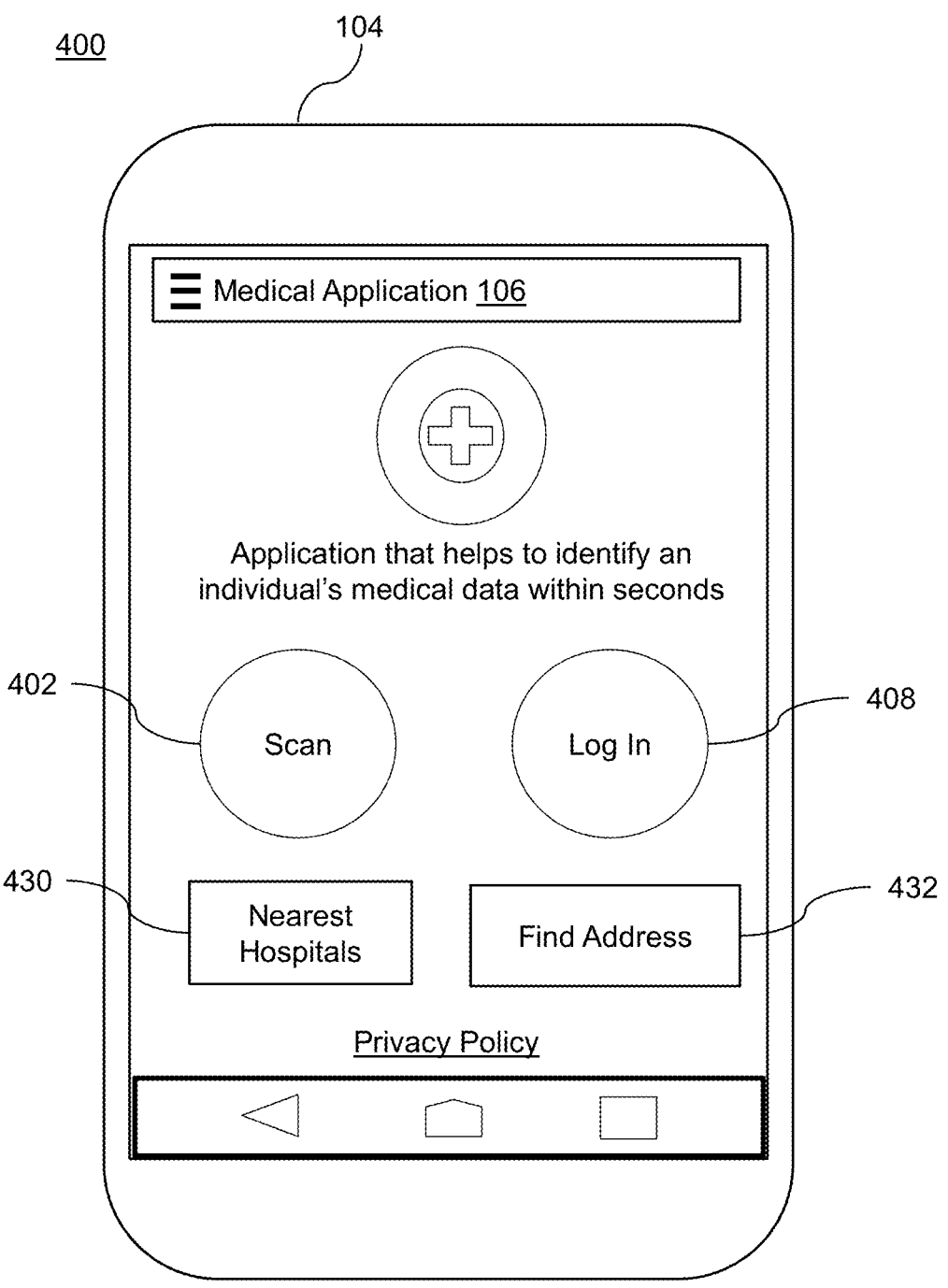
FIG. 4A illustrates a graphical user interface of a medical application on a user device and/or a medical personnel device, according to an exemplary embodiment of the present invention.
Figure 4B:
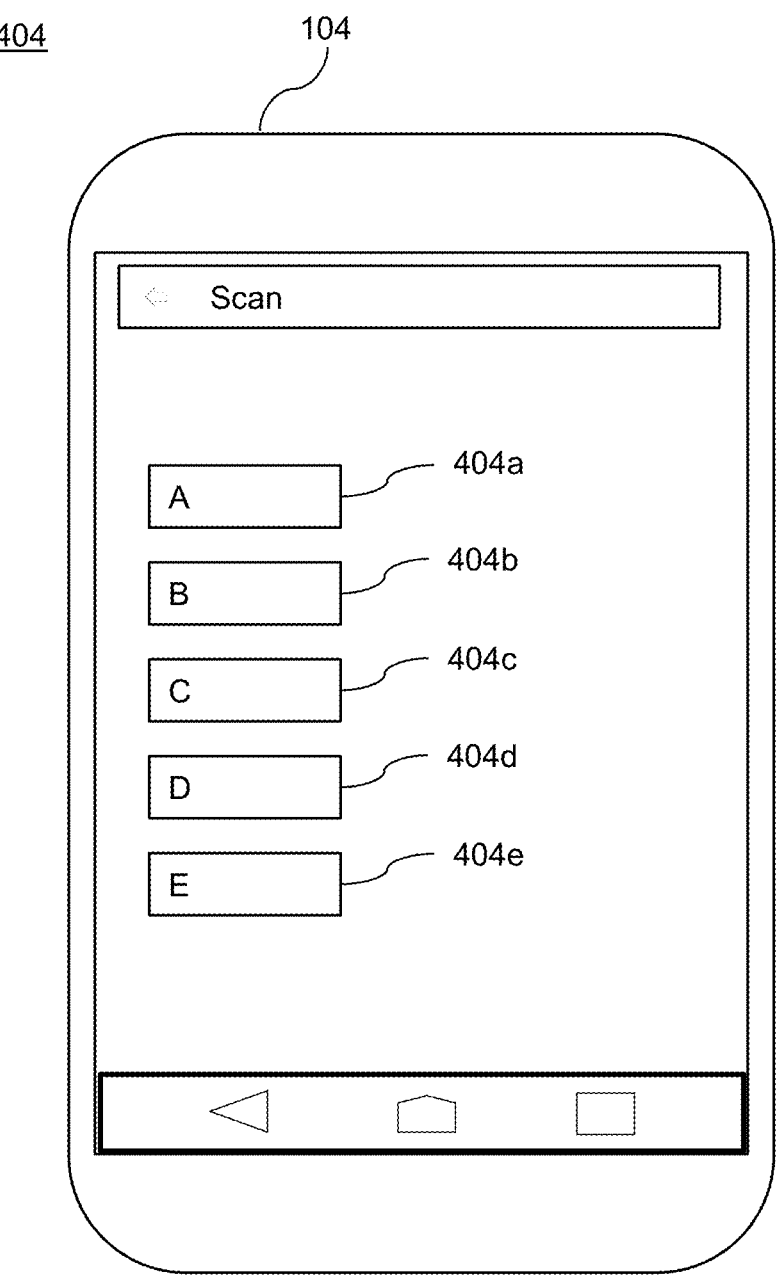
FIG. 4B illustrates a graphical user interface of the medical application wherein different scan options are presented, according to an exemplary embodiment of the present invention.
Figure 4C:
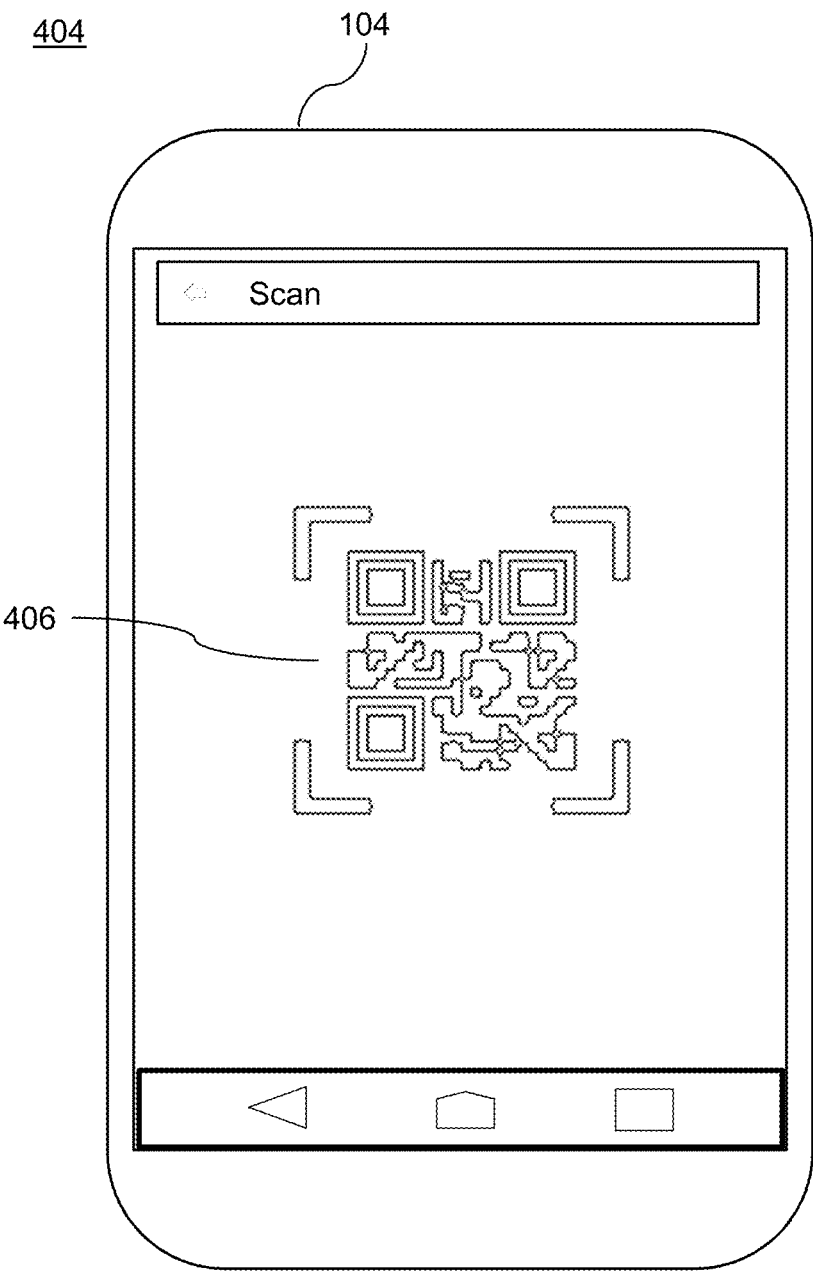
FIG. 4C illustrates a graphical user interface of the medical application wherein the user scans a first medical identifier, according to an exemplary embodiment of the present invention.

FIG. 4A illustrates a graphical user interface 400 of a medical application 106 on a user device 104 for medical purpose, according to an exemplary embodiment of the present invention. A "scan" button 402 is used by the user for scanning purposes. When a user clicks on the "scan" button 402, a user interface 404 is displayed on the user device 104, as shown in FIG. 4B. A number of scanning options 404*a*-404*e* are displayed on the user device 104, which may include, but not limited to, a first medical identifier (e.g., QR code), a Radio Frequency Identification (RFID), a biometric such as, but not limited to, a fingerprint, an iris scan, a face ID, an eye scan, a DNA scan, and so forth, of a patient. In an embodiment of the present invention, the personnel may use a camera of the user device 104 to scan the identification code and the biometric of the individual. The personnel may scan the real-time biometric such as a fingerprint 428, of the individual and the identification code of the individual as shown in FIG. 4G. In an embodiment of the present invention, the user may use a camera of the user device 104 to scan the first medical identifier. In case, the user desires to scan the first medical identifier, then a QR code 406 associated with a patient is scanned by the user device 104, as shown in FIG. 4C. Therefore, the user may then be able to access a set of medical data in a readable format as per the level of authorization. Once the QR code 406 is scanned, an unprotected PII data, a protected PII data, a basic PHI data, or a combination thereof, associated with the patient is displayed on the user device 104, which may include, a first name, a last name, an emergency contact, a date of birth, a gender, and so forth. In case, the user scans the QR code by any scanning application and/or device (other than the user device 104), then the unprotected PII data of the patient may be displayed in a data string, for example, PII % NAME % DOB % ADDRESS % CONTACTNUMBER % MESSAGEFOREMERGENCY CONTACT % PHI % NUMBER.

Figure 4D:
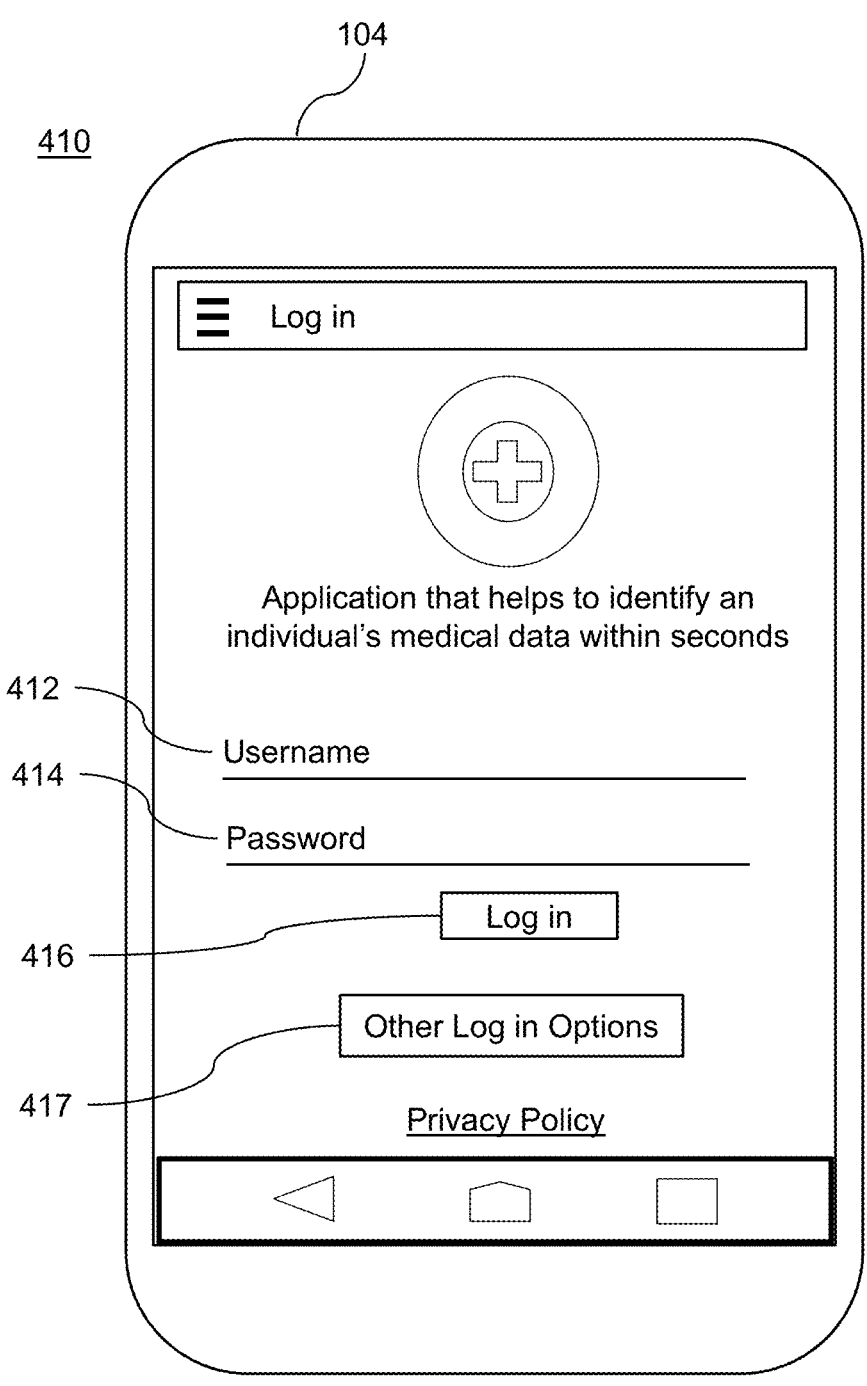
FIG. 4D illustrates a graphical user interface of the medical application wherein a user logs-in by using log-in credentials, according to an exemplary embodiment of the present invention.
Figure 4E:
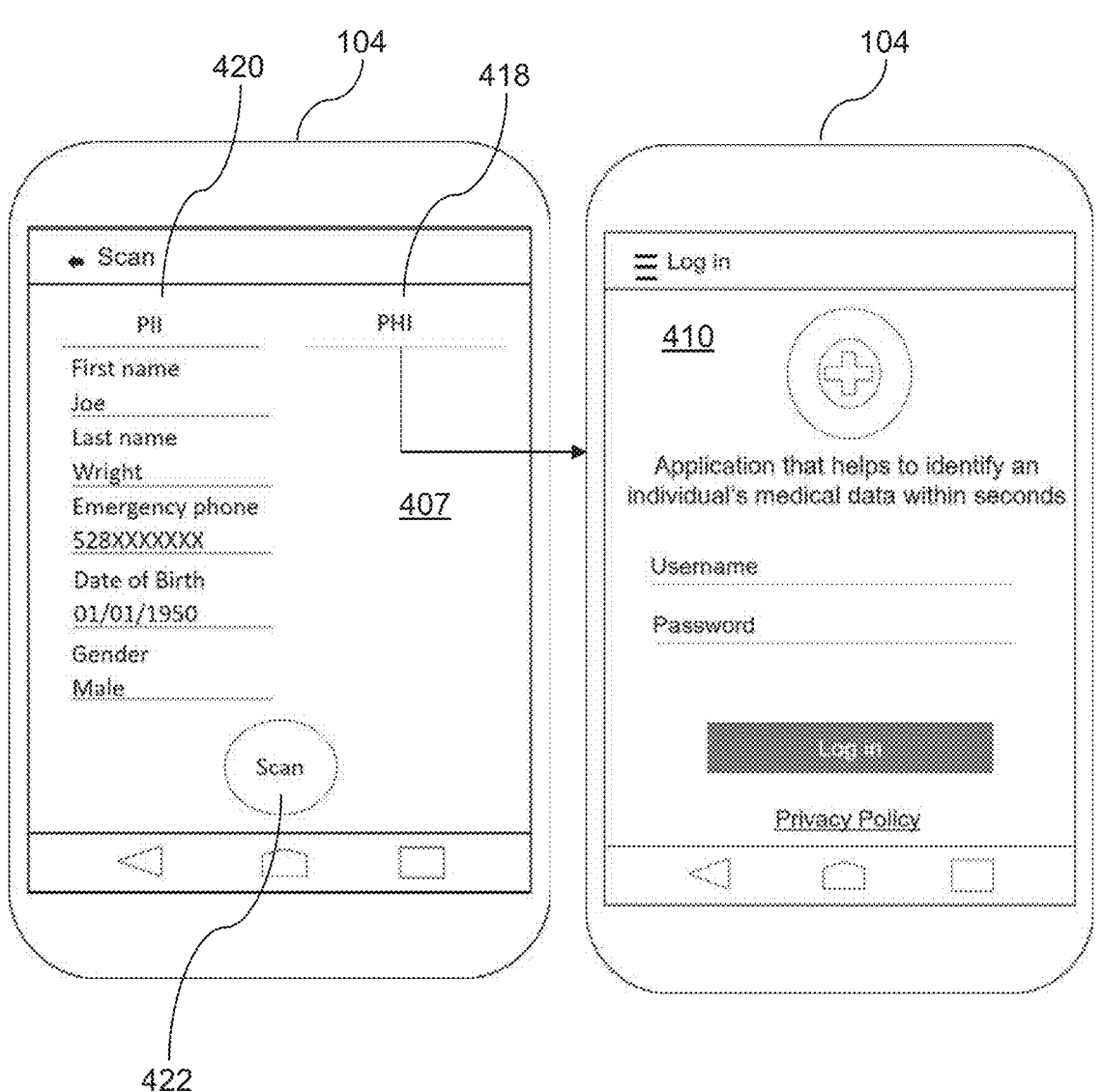
FIGS. 4E, 4F and 4G illustrate a graphical user interface of the medical application wherein the user accesses a set of the medical data associated with a patient, according to an exemplary embodiment of the present invention.
Figure 4F:
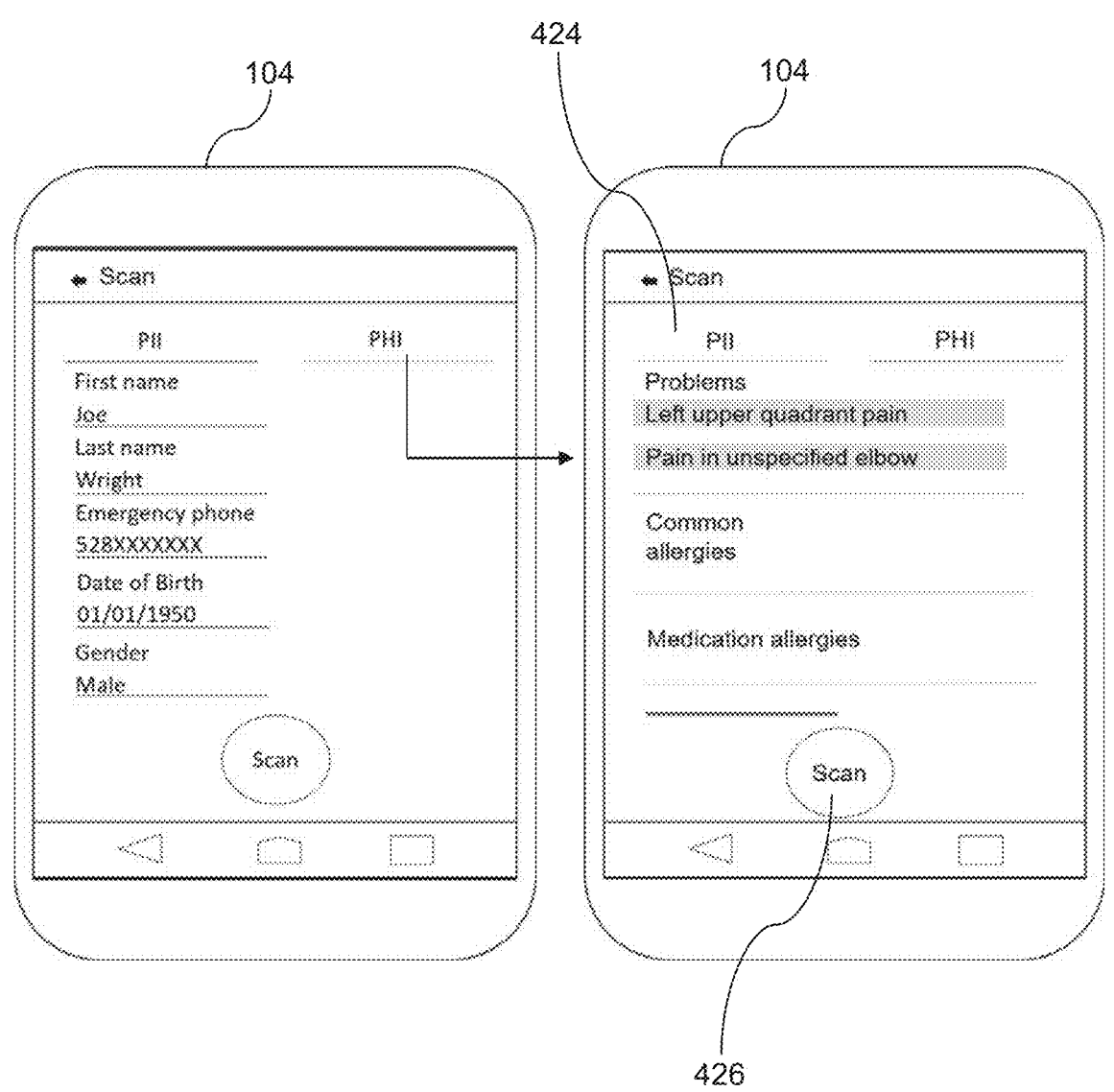
Figure 4G:
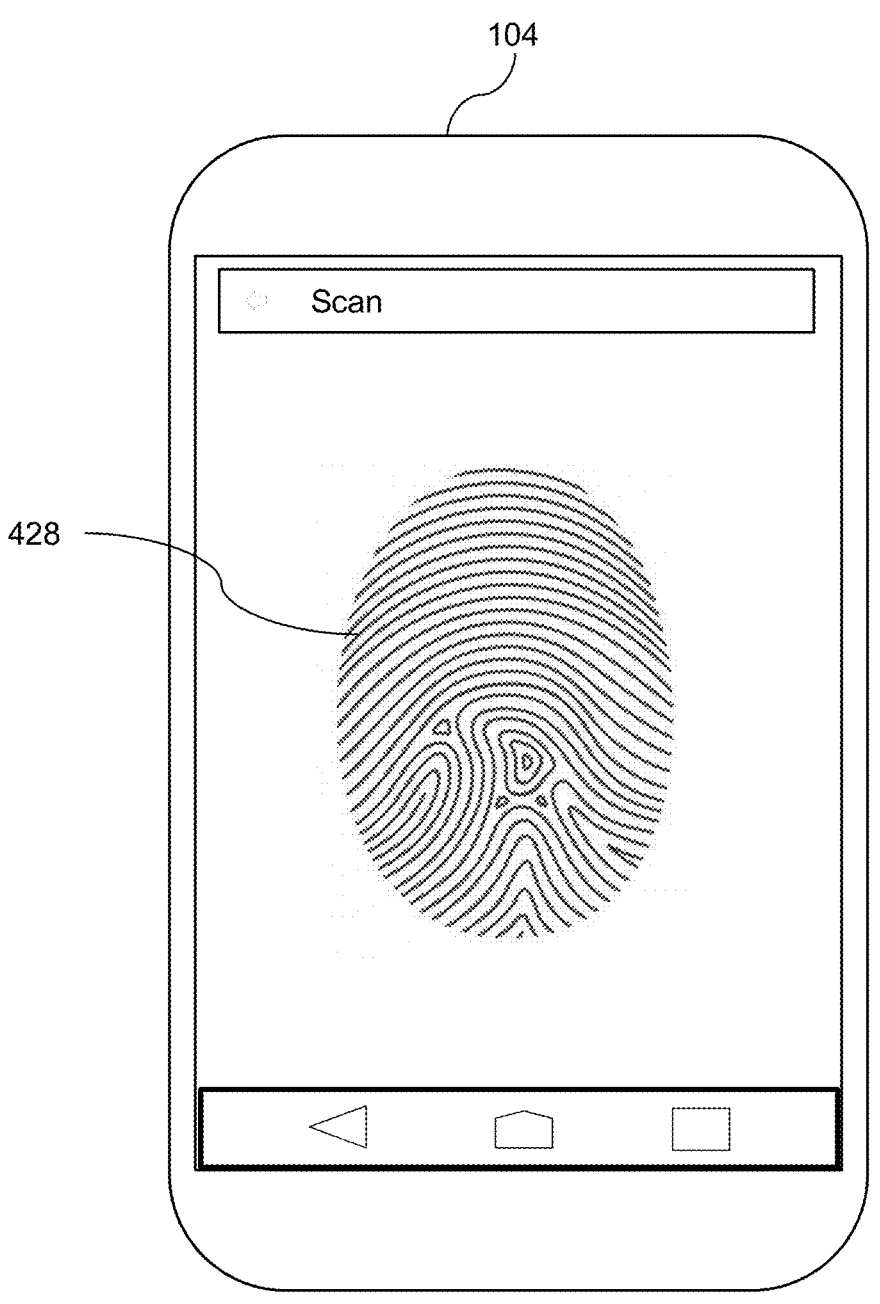

In order to log-in the medical application 106, the user may click on a "log-in" button 408 as shown in the FIG. 4A, which may redirect the user to a graphical user interface 410 as shown in FIG. 4D. In an embodiment of the present invention, the "log in" button 408 may be used to authorize a user who desires to access the protected medical data in order to provide medical treatment to the patient in an emergency condition. In an embodiment of the present invention, the user log-in into the medical application 106 by providing log-in credentials such as, a username 412, and a password 414. After entering the log-in credentials, a "Log-in" button 416 is pressed. In another embodiment of the present invention, the user may log-in into the medical application 106 by clicking on an "other log-in option" button 417, in which the user may provide a unique identifier, or any other log-in credentials. Embodiments of the present invention may cover or intend to include any log-in option, including known, related art, or later developed technologies to log-in into the medical application 106. The log-in credential of the user is required to identify the user and to determine which data fields are to be made visible to the user based on a level of authorization defined by the patient. By clicking on the "Log-in" button 416, the electronic session may be extended for a regulated amount of time in compliance with HIPAA. In an offline mode, the user, as per the level of authorization, may not be able to access and/or download the protected medical data associated with the patient. In addition, by clicking on a "I forgot my credentials" button (not shown), a notification may be displayed on the user interface 410 for how to restore the credentials.

Further, a user interface displaying a "PII" tab 420 and a "PHI" tab 418 is shown on the user device 104. In case, the user is not logged in the medical application 106 and the user clicks on the "PII" tab 420, then the unprotected PII data of the patient is displayed on the user device 104. In case, the user is logged in the medical application 106 and the user clicks on the "PII" tab 420, then the protected PII data along with the unprotected PII data of the patient is displayed on the user device 104.

In case, the user is not logged in the medical application 106 and the user clicks on the "PHI" tab 418, then the user is redirected to the user interface 410 to first log-in into the medical application 106 to access the protected medical data. Once, the user is logged in the medical application 106, then the basic PHI data 424 is displayed on the user device 104 even in an offline mode.

Further, in order to access the extended PHI data of the patient, the user needs to scan a unique identifier such as, but not limited to, a biometric of the patient. Embodiments of the present invention may cover or intend to include any other unique identifier, including known, related art, or later developed technologies to provide access to the user for extended PHI data. The user may then clicks on a "scan" button 426, as shown in the FIG. 4F. A fingerprint 428 of the patient is scanned as shown in FIG. 4G, which may be used to identify the patient and then to provide access to the extended PHI data to the user. The identification of the patient may include, but not limited to, a name, a primary language, a secondary language, a department, a service branch, a status, a rank (e.g., Major General, etc.), and so forth. In an embodiment of the present invention, the fingerprint of the patient may be used as a URL to authorize the user of the user device 104 to access the extended PHI data stored in the EHR database 111.

In reference to the FIG. 4A, the patient and/or the user may find nearest hospitals within the medical application 106 by clicking on a "nearest hospital" button 430. In order to search for a nearest hospital, the patient device 102 and/or the user device 104 should be in an online mode. In addition, the patient and/or the user may find an address on the medical application 106 by clicking on a "find address" button 432. Further, additional options such as, a possibility to renew license, a quick navigation to "nearest hospitals", a "find address" functionality, a log out option, etc. may be displayed by clicking on a "menu" button (not shown) on the medical application 106.

Figure 5A:
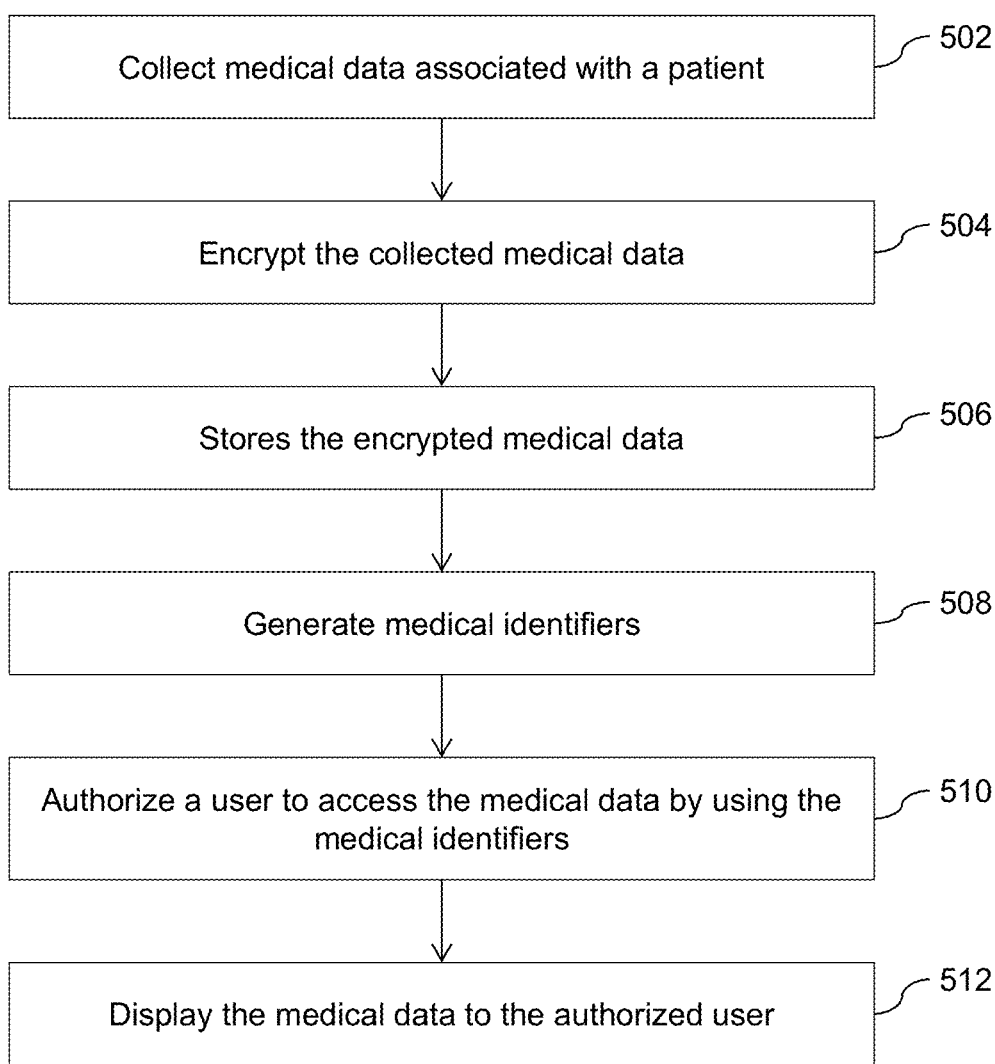
FIG. 5A is a flowchart of a method for communicating medical data of a patient to a user, according to an embodiment of the present invention.

FIG. 5A is a flowchart of a method 500 for communicating medical data of a patient to a medical personnel, according to an embodiment of the present invention.

At step 502, the health care platform 108 may collect medical data associated with a patient. The medical data may include, but not limited to, a PII Data and a PHI data. As discussed above, the PII data may include, but not limited to, a name, an address, a date of birth, a contact information, social security number, employee ID, types of identification allergies, types of implants, person being Alzheimer's, common medication, any other common and rarely changeable health information specifics of an industry (e.g., military, police force, etc.), current and past diagnosis and medications, and so forth. Further, the PHI data may include, but not limited to, a blood type and RH factor, a diabetes type, allergies, implanted devices, a medical code status, a link to a database, a common organ donor, Alzheimer's type of specific data based on a user's requirement and specifics of an industry, and so forth. In addition, the health care platform 108 may categorize the medical data based on factors, such as, but not limited to, personal data, medical data, level of sharing defined by the patient, HIPAA laws, and so forth.

At step 504, the health care platform 108 may encrypt the medical data collected from the patient. The medical data may be encrypted in order to eliminate unauthorized access to the medical data. Further, at step 506, the health care platform 108 may store the medical data in one or more databases, such as, the EHR database 111.

Next, at step 508, the health care platform 108 may generate medical identifiers based on the medical data collected from the patient. A first medical identifier may be generated, which may be used to access a first set of the medical data. In addition, a second medical identifier may be generated, which may be used to access a second set of the medical data only in an online mode. A second set of the medical data may be embedded as a web link in the second medical identifier, for example, a URL to a database that stores a second set of the medical data, which may include, but not limited to, extended PHI data. In an embodiment of the present invention, the second medical identifier may be, but not limited to, a unique identifier, such as, but not limited to, a fingerprint of the patient.

Further, at step 510, the health care platform 108 may authorize a user to access the medical data by using the medical identifiers, in an embodiment of the present invention. The health care platform 108 may authorize the user based on log-in credentials. The authorization of the user is done in an online mode on the user device 104. Once, the user is authorized, the health care platform 108 may display the medical data to the user, at step 512. In order to display the medical data, the user may scan the first medical identifier by using any OCR device to access the unprotected PII data. Further, to access the protected PII data, basic PHI data, and/or the extended PHI data, the user may first have to scan the QR code with the medical application 106 installed on the user device 104 and then clicks on the URL link and/or may scan the fingerprint of the patient, which directs the user to a web portal, such as, an Electronic Health Record (EHR) portal that displays the medical data. The extended PHI data may be accessed by the user device 104 in an online mode only.

FIG. 5B is a flowchart of a method 550 for validating an identity of an individual by a personnel, according to another embodiment of the present invention.

At step 552, the health care platform 108 may collect identification data of an individual. The identification data may include, but not limited to, personal data (e.g., a name, an age, a gender, a photograph of the individual, etc.), biometric data, demographic data, and so forth of the user. In an embodiment of the present invention, the biometric data may be for example, but not limited to, a fingerprint data, an iris data, and so forth.

At step 554, the health care platform 108 may encrypt the data collected from the individual. The identification data may be encrypted in order to eliminate unauthorized access to the identification data of individuals. Further, at step 556, the health care platform 108 may store the identification data in one or more databases, such as, the EHR database 111.

At step 558, the health care platform 108 may generate an identification code for the individual. The identification code may be embedded with the identification data of the individual. Further, the generated identification code may be printed on an article associated with the individual. As discussed above, the article may be, but not limited to, a wristband, a dog tag, a driving license, a passport, a car windshield, a credit card, a ID card, a wearable jewelry, a refrigerator magnet, a chain, a mobile phone, a helmet, and so forth. Embodiments of the present invention may cover or intend to include any type of an article that the patient carries at most/every time.

Further, at step 560, the health care platform 108 may enable an authorized personnel to scan the generated identification code of the individual, at a secured place. In an embodiment of the present invention, the authorized personnel may scan the identification code by using the medical application 106. In addition, the health care platform 108 may enable the authorized personnel to scan a real-time biometric of the individual.

At step 562, the health care platform 108 may enable the authorized personnel to validate the identity of the individual when the scanned identification code of the individual matches with the scanned real-time biometric of the individual.

Next, at step 564, the health care platform 108 may enable the authorized personnel to access medical data of the individual (if required), only when the identity of the individual is valid. At step 566, the health care platform 108 may display the identity and the medical data to the authorized personnel.

In an exemplary scenario, a person A arrives at a foreign custom counter in a foreign country. A law officer at the custom counter receives identification data such as, but not limited to, a name, an age, biometric data (e.g., a fingerprint, an iris scan, etc.) etc.; and medical data such as, PII data. The scanned biometric data is then encoded into an identification code generated for the person A. The generated identification code is then printed on a label and a wristband. The label is attached to a passport of the person A, along with entry Visa stamp, while the wristband with the identification code is being provided to the person A as a wearable item. During security checks at secured places such as, an airport, a religious place, police stations, high security areas, etc. a local police officer may scan the identification code provided on the wristband along with biometric scanned at real time by using the medical application 106 to identify a positive identity of the person A.

In another exemplary scenario, during a recruitment process into military, police, firefighters and/or other unions, identification data (for example, a name, an age, a gender, biometric data such as, a fingerprint) and medical data (PII and PHI data) are collected. The collected identification data and the medical data are encoded into an identification code generated for each candidate. The generated identification code is then printed on a label, a wristband, an ID card, etc. or any other wearable article. Then, during emergency situations or medical procedures, an identity of a person is positively identified by scanning the generated identification code and real time biometrics of the person by the medical application 106. Therefore, these procedures may add an extra level of security and may also minimize potential errors due to misidentification. In addition, this process may expedite time required to identify an individual and access the medical data associated with the individual.

Figure 6:
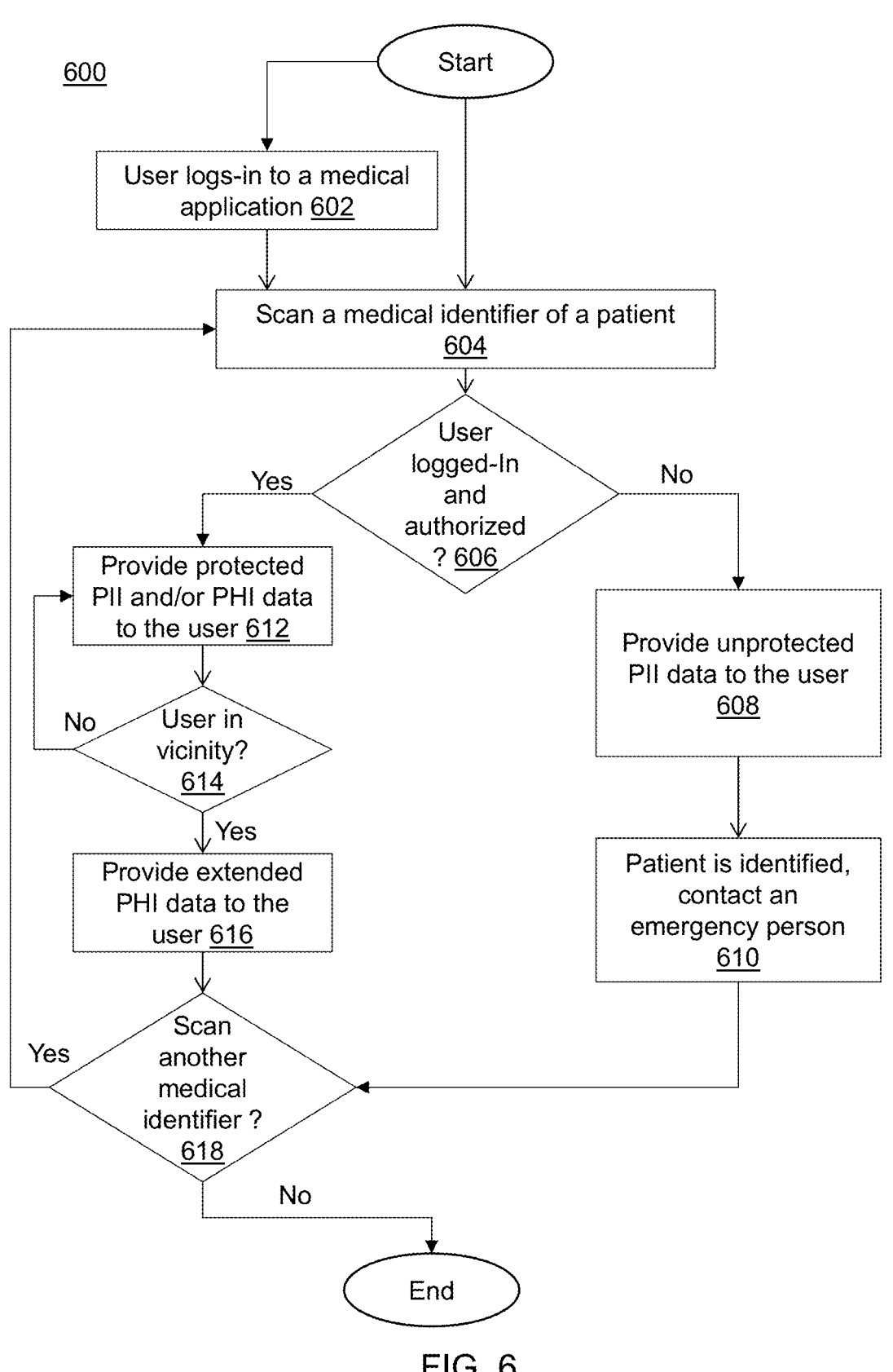
FIG. 6 is a flowchart of a method for communicating medical data of a patient to a user when the patient met with an accident, according to another embodiment of the present invention.

FIG. 6 is a flowchart of a method 600 for communicating medical data of a patient to a user when the patient met with an accident, according to another embodiment of the present invention.

At step 602, the user logs-in to the medical application 106. The log-in of the user in the medical application 106 may be required for the identification and/or authorization of the user. The user may log-in the medical application 106 by using log-in credentials, such as, but not limited to, a log-in ID and a password, and/or a unique identifier, for example, a fingerprint, a face recognition, retina, and so forth. Embodiments of the present invention are intended to include or otherwise cover any type of unique identifier, including known, related art, and/or later developed technologies to securely log-in into the medical application 106. In addition, the user may automatically logs-off from the medical application 106 after a preset period of time. In an embodiment of the present invention, the user may automatically logs-off from the medical application 106 when an electronic session between the user device 104 and the EHR database 111 is terminated, due to, for example, but not limited to, inactivity for a preset period of time, HIPAA laws and regulations, and so forth.

Optionally, the user may skip the step 602 and proceeds to a step 604, where the user scans a medical identifier of a patient using the medical application 106 on the user device 104. In an embodiment of the present invention, the medical identifier may be but not limited to, a QR code, a bar code, a unique identifier, and so forth, which may be attached and/or printed on an article such as, but not limited to, a driving license, a helmet, credit card, and so forth.

Further, at step 606, it is determined whether the user is logged-in the medical application 106 on the user device 104. In case, it is determined that the user is not logged-in the medical application 106, that is the user is in an offline mode, then the method 600 proceeds towards a step 608 and provide an unprotected PII data to the user. Further, a unique identifier, such as a biometric of the patient may also be scanned for the identification of the patient at step 610. In addition, using the unprotected PII data and/or the identification of the patient, an emergency contact person associated with the patient may be contacted.

Next, at the step 606, in case it is determined that the user is logged-in the medical application 106 on the user device 104, that is the user is in an online mode, and is authorized as per the patient's HIPAA settings, then protected PII data and/or PHI data may be provided to the user based on the user's credentials and the patient's HIPAA settings, at step 612. In case, the user is a first responder, then the first responder may browse between various PII data fields and PHI data fields and may use other functions of the medical application 106. In an embodiment of the present invention, some of the critical medical data of the patient is available even in an offline mode to the first responder. In case, the user is a medical personnel, then the PII data and the PHI data of the patient is accessed by the medical personnel in an online mode.

Further, at step 614, it is determined whether the user is in the vicinity of a medical facility. In case it is determined that the medical personnel is present within the vicinity of the medical facility, then the authorized medical personnel may access the extended PHI data by using a unique identifier and/or other identification techniques of the patient, at step 616. In an embodiment of the present invention, the vicinity of a medical facility may be, but not limited to, an emergency room, a hospital, a clinic, and so forth and should be in an online mode.

In case, it is determined that the user is not present within the vicinity of the medical facility, then the user may access only the protected PII data and the PHI data.

Further, at step 618, it is determined whether a medical identifier associated with a second patient is to be scanned. In case, it is determined that a medical identifier associated with the second patient is to be scanned, then the method 600 returns to the step 604 and scans the medical identifier of the second patient. Otherwise, the method 600 terminates.

In an embodiment of the present invention, the medical identifier may be used for security protection. In an exemplary scenario, each member of a Church or a Synagogue is provided with a medical identifier by a security agency. When a person desires to enter the Church or the Synagogue, the medical identifier may be scanned by a scanning device such as, but not limited to a, mobile device to authenticate that the person is a member of the congregation and therefore, based on the authentication, the person may further be authorized to enter or deny access to the premises. This may prevent any unauthorized activities within the premises, such as, but not limited to, shooting, robbery, and so forth.

In another exemplary scenario, a medical identifier is generated for each student. In case of an emergency situation, the medical data (e.g., PII data, or PHI data) associated with a student may be accessed to provide medical treatment to the student.

Figure 7B:
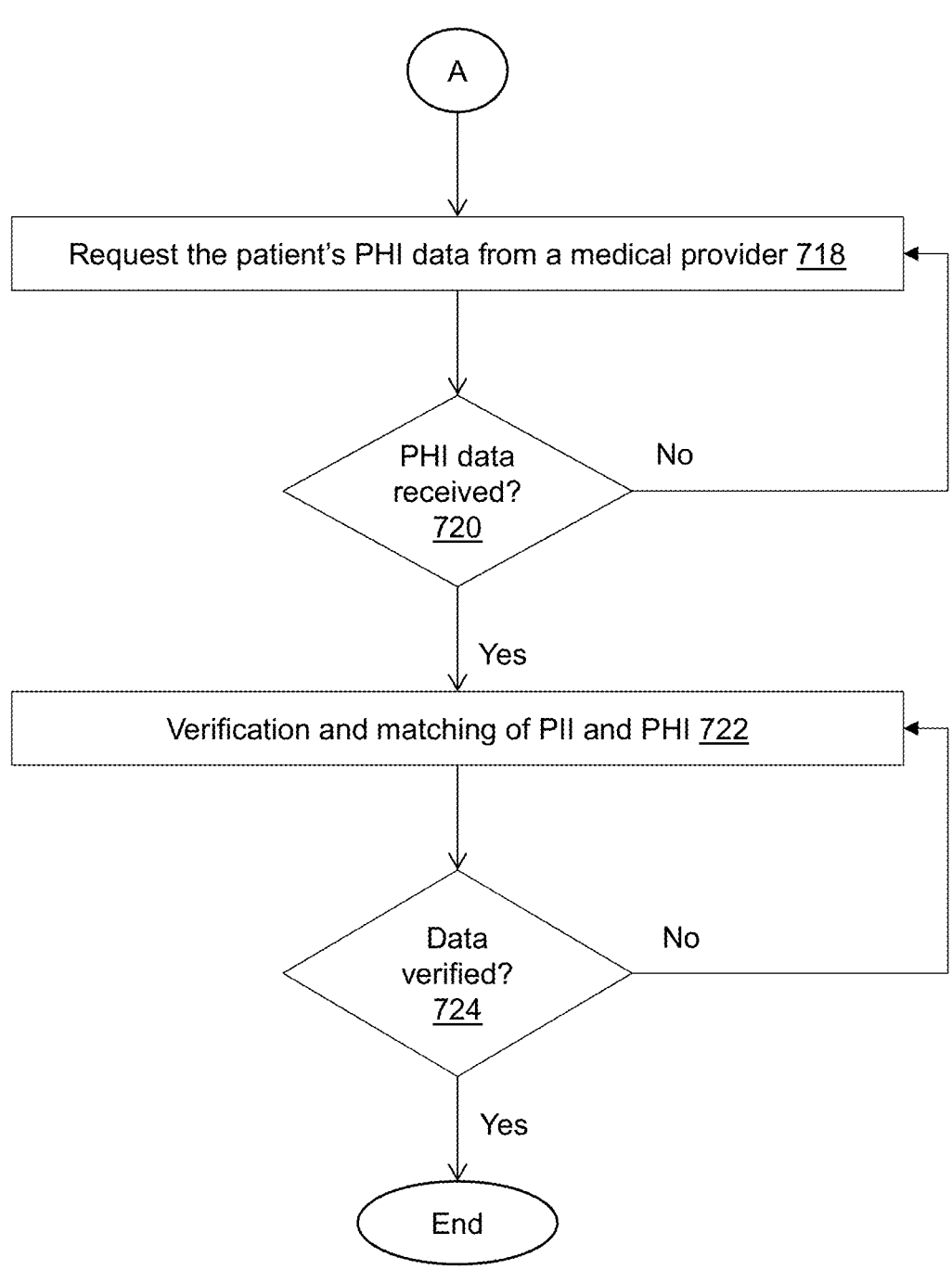

FIGS. 7A and 7B are flowcharts of a method 700 for registering a patient and collecting medical data for records for providing healthcare service to the patient, according to an embodiment of the present invention.

At step 702, the health care platform 108 familiarizes with a profile and needs of a patient. In an embodiment of the present invention, the profile and needs may include data such as, but not limited to, a name, an address, a date of birth, a contact information, a social security number, an employee ID, types of identification allergies, types of implants, a person being Alzheimer's, common medication, any other common and rarely changeable health information specifics of an industry (e.g., military, police force, etc.), and so forth. In another embodiment of the present invention, the profile and needs may include a level of sharing of the medical data with users, as discussed in the FIG. 2.

At step 704, the health care platform 108 customizes the medical application 106 for the patient, according to an embodiment of the present invention. Further, at step 706, the health care platform 108 provides a training to the patient or a representative of the patient to use the medical application 106 as and when required such as, in case of an emergency situation.

Further, at step 708, the health care platform 108 requests data from the patient. In an embodiment of the present invention, the data may include PII data such as, but not limited to, a name, an address, a date of birth, a contact information, a social security number, an employee ID, types of identification allergies, types of implants, a person being Alzheimer's, common medication, any other common and rarely changeable health information specifics of an industry (e.g., military, police force, etc.), and so forth.

At step 710, the health care platform 108 determines whether the data is received from the patient or not. In case, the health care platform 108 determines that the data is not received, then the method 700 returns the step 708 and again requests for the data from the patient. In case, the health care platform 108 determines that the data is received, then the method 700 proceeds towards a step 712.

Next, at the step 712, the health care platform 108 creates a profile for the patient. The profile may include the data, such as the PII data, shared by the patient, in an embodiment of the present invention. In addition, after creating the profile, the health care platform 108 sends a login credentials to the patient. The log-in credentials may be, such as, but not limited to, a sign-in ID and a password, and/or a unique identifier, for example, a fingerprint, a face recognition, retina, etc. Embodiments of the present invention are intended to include or otherwise cover any type of log-in credentials, including known, related art, and/or later developed technologies to securely log-in into the medical application 106.

At step 714, the health care platform 108 may create a medical record release form and requests the patient to sign it, in an embodiment of the present invention. The medical record release form may authorize a medical personnel to share medical information with the health care platform 108.

At step 716, the health care platform 108 determines whether the medical record release form is signed by the patient. In case, the health care platform 108 determines that the medical record release form is not signed, then the method 700 returns to the step 714 and the health care platform 108 again sends a request to the patient to sign the medical record release form. In case, the health care platform 108 determines that the medical record release form is signed by the patient, then the method 700 proceeds towards a step 718.

At the step 718, the health care platform 108 requests PHI data from the medical personnel, in an embodiment of the present invention. The PHI data may include, but not limited to, a blood type, a diabetes type, allergies, implanted devices, a medical code status, a common organ donor, Alzheimer's type of specific data based on a user's requirement and specifics of an industry, and so forth.

Further, at step 720, the health care platform 108 determines whether the PHI data is received or not. In case the health care platform 108 determines that the PHI data is not received, then the method 700 returns to the step 718 and the health care platform 108 may send a request to the medical personnel for the PHI data. In case, the health care platform 108 determines that the PHI is received, then the method 700 proceeds towards a step 722.

At the step 722, the health care platform 108 may verify and match the PII data and the PHI data, in an embodiment of the present invention. Further, at step 724, the health care platform 108 determines whether the data is verified or not. In case, the health care platform 108 determines that the data is not verified, then the method 700 returns to the step 722 and verifies the data. In case, the health care platform 108 determines that the data is verified, then the method 700 concludes.

Figure 8:
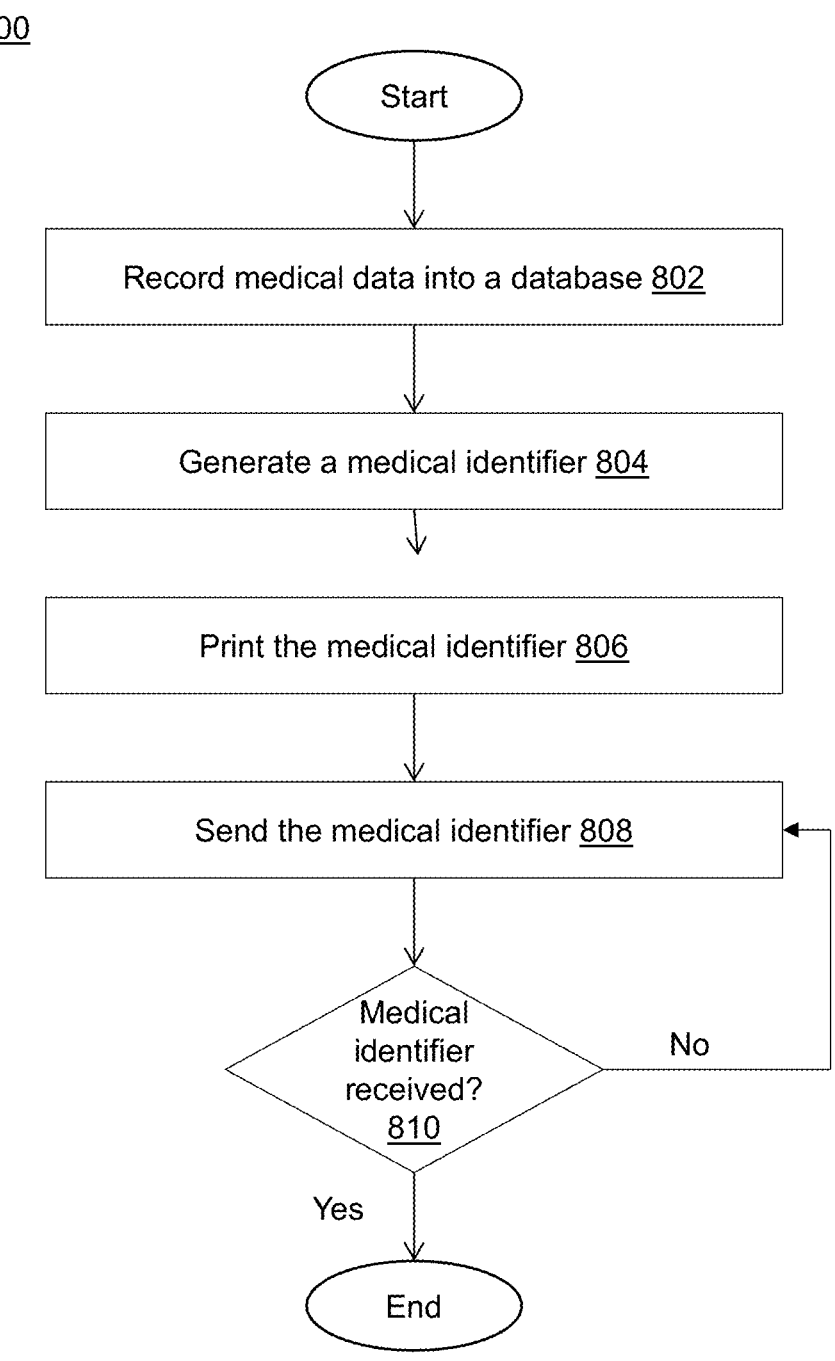
FIG. 8 is a flowchart of a method for creating medical records and generating a medical identifier for a patient, according to an embodiment of the present invention.

FIG. 8 is a flowchart of a method 800 for creating medical records and generating a medical identifier for the patient, according to an embodiment of the present invention.

At step 802, the health care platform 108 records the medical data into a database, in an embodiment of the present invention. The health care platform 108 may record or store the verified data, from the FIG. 7, into a database such as, the EHR database 111.

Further, at step 804, the health care platform 108 generates a first medical identifier for the patient, in an embodiment of the present invention. In an embodiment of the present invention, the first medical identifier may be, but not limited to, a Quick Response (QR) code, a bar code, and so forth. The first medical identifier may be scanned by any Optical Character Recognition (OCR) device, such as, but not limited to, a scanner, a smart phone, a mobile device, and so forth. In another embodiment of the present invention, the health care platform 108 may generate a second medical identifier that may be used to access a second set of the medical data in an online mode only, as discussed in the FIG. 3. The second medical identifier may be, but not limited to, a Uniform Resource Locator (URL).

Next, at step 806, the health care platform 108 may print the generated first medical identifier and send the printed medical identifier to the patient, at a step 808.

At step 810, the health care platform 108 determines whether the medical identifier is received by the patient or not. In case, the health care platform 108 determines that the medical identifier is not received by the patient, then the method 800 returns to the step 808 and send the medical identifier again. In case, the health care platform 108 determines that the medical identifier is received by the patient, then the method 800 concludes.

Figure 9:
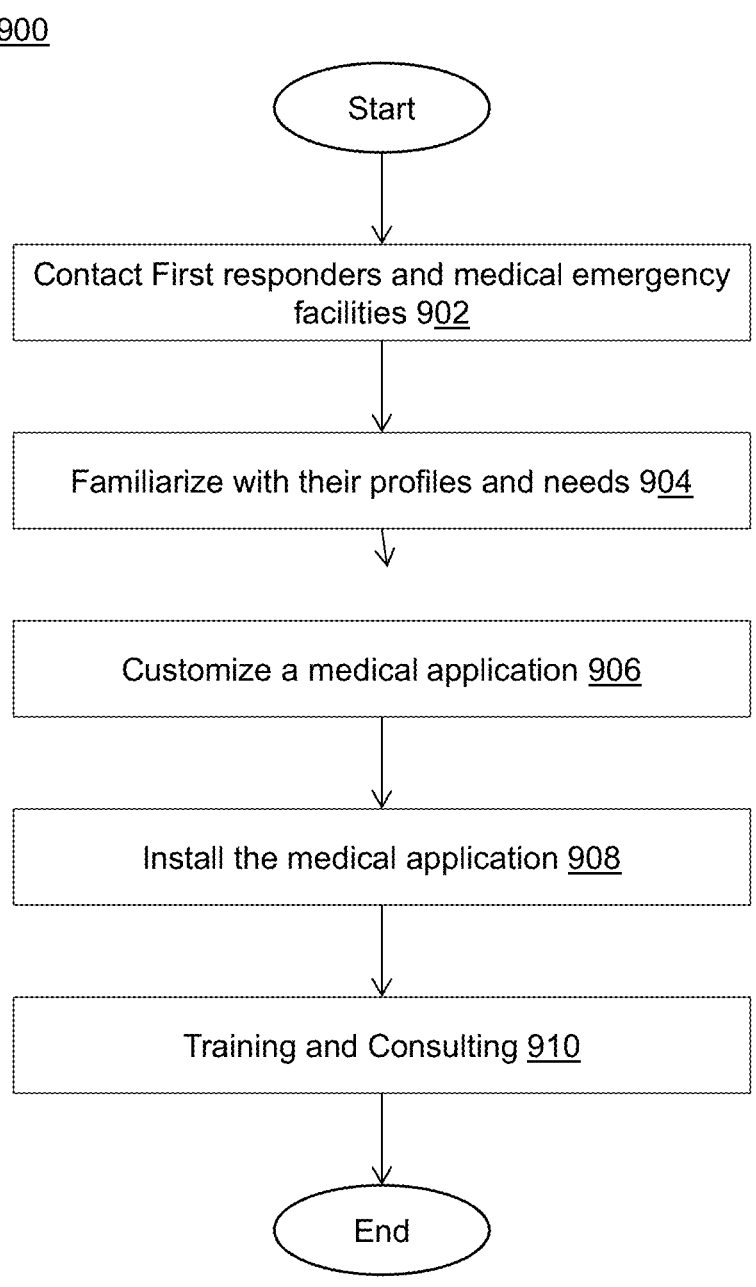
FIG. 9 is a flowchart of a method for collecting data of medical personnel, according to an embodiment of the present invention.

FIG. 9 is a flowchart of a method 900 for collecting data of medical personnel, according to an embodiment of the present invention. At step 902, the health care platform 108 contacts one or more medical personnel and medical emergency facilities. Next, at step 904, the health care platform 108 familiarized with profiles and needs of the one or more medical personnel and medical emergency facilities. The profile of the one or more medical personnel and medical emergency facilities may include, but not limited to, a name, an email id, a contact number, a medical ID, and so forth.

Further, at step 906, the health care platform 108 may customize the medical application 106 for the usage of the medical personnel, in an embodiment of the present invention. The customization of the medical application 106, may include, but not limited to, a list of patients, medical records of patients, and so forth.

At step 908, the health care platform 108 may install the medical application 106 on the user device 104, in an embodiment of the present invention.

Furthermore, at step 910, the health care platform 108 may provide training and consulting to the medical personnel about the usage of the medical application 106, in an embodiment of the present invention. The training may include, but not limited to, scanning a medical identifier of a patient, retrieving its medical records, updating the medical records, contacting an emergency contact person of a patient, and so forth.

FIG. 10 is a flowchart of a method 1000 for updating medical data of a patient in a database, according to an embodiment of the present invention.

At step 1002, the health care platform 108 may update the patient profile, in an embodiment of the present invention. The updating of the profile, may include, updating contact information, updating medical data, and so forth.

At step 1004, the health care platform 108 requests PHI data from a medical provider, in order to update the patient profile, in an embodiment of the present invention. The medical provider may be, but not limited to, a medical personnel of a Medical Emergency Facility (MEF), which provides medical services to the patient.

At step 1006, the health care platform 108 determines whether the PHI data is received or not. In case, the health care platform 108 determines that the PHI data is not received, then the method 1000 returns the step 1004 and again requests for the PHI data from the medical provider. In case, the health care platform 108 determines that the PHI data is received, then the method 1000 proceeds towards a step 1004.

At the step 1004, the health care platform 108 verifies and matches the medical data of the patient, in an embodiment of the present invention. The medical data may include the PII data and the PHI data. The health care platform 108 may match the PII data and the PHI data stored in the EHR database 111 with the medical data received from the patient and the medical personnel.

Further, at step 1010, the health care platform 108 determines whether the data is correct and matches with the medical data stored in the EHR database 111. In case, the health care platform 108 determines that the medical data stored in the EHR database 111 matches with the received medical data, then the method 1000 returns to the step 1004 and requests for the medical data from the medical personnel. In an embodiment of the present invention, the health care platform 108 may request for the medical data after a predefined time interval. The predefined time interval may be, every three days, weekly, bi-weekly, monthly, and so forth. In case, the health care platform 108 determines that the medical data is changed, then the method 1000 proceeds towards a step 1012.

At the step 1012, the health care platform 108 generates a new medical identifier for the patient, in an embodiment of the present invention. The new medical identifier may include, but not limited to, the updated medical data. Further, the health care platform 108 sends the generated medical identifier to the patient, in an embodiment of the present invention.

Techniques disclosed herein may be useful for identification purposes, such as for border control and/or to combat human trafficking. For example, an identifier (e.g., a QR code) may be used to identify whether a person is involved in human trafficking based on data in a government database (e.g., Homeland Security). In this example, the medical identifier is used for identification purposes. The mechanism or operation of the product/service may be similar to other examples provided herein, but the agency/operator and cases of usage/applications may differ. The product/service may contain/utilize information related to a certain person and if this person (when he/she crosses the borders) under another name, the product can identify the personality. Moreover, this information can help to compare the data with data in a government database (e.g., a Homeland Security database). In this way, a government agency may identify particular people (e.g., a person designated as a member of a high-risk group, or a person known or suspected of being involved in human trafficking or other illicit activity).

Figure 11:
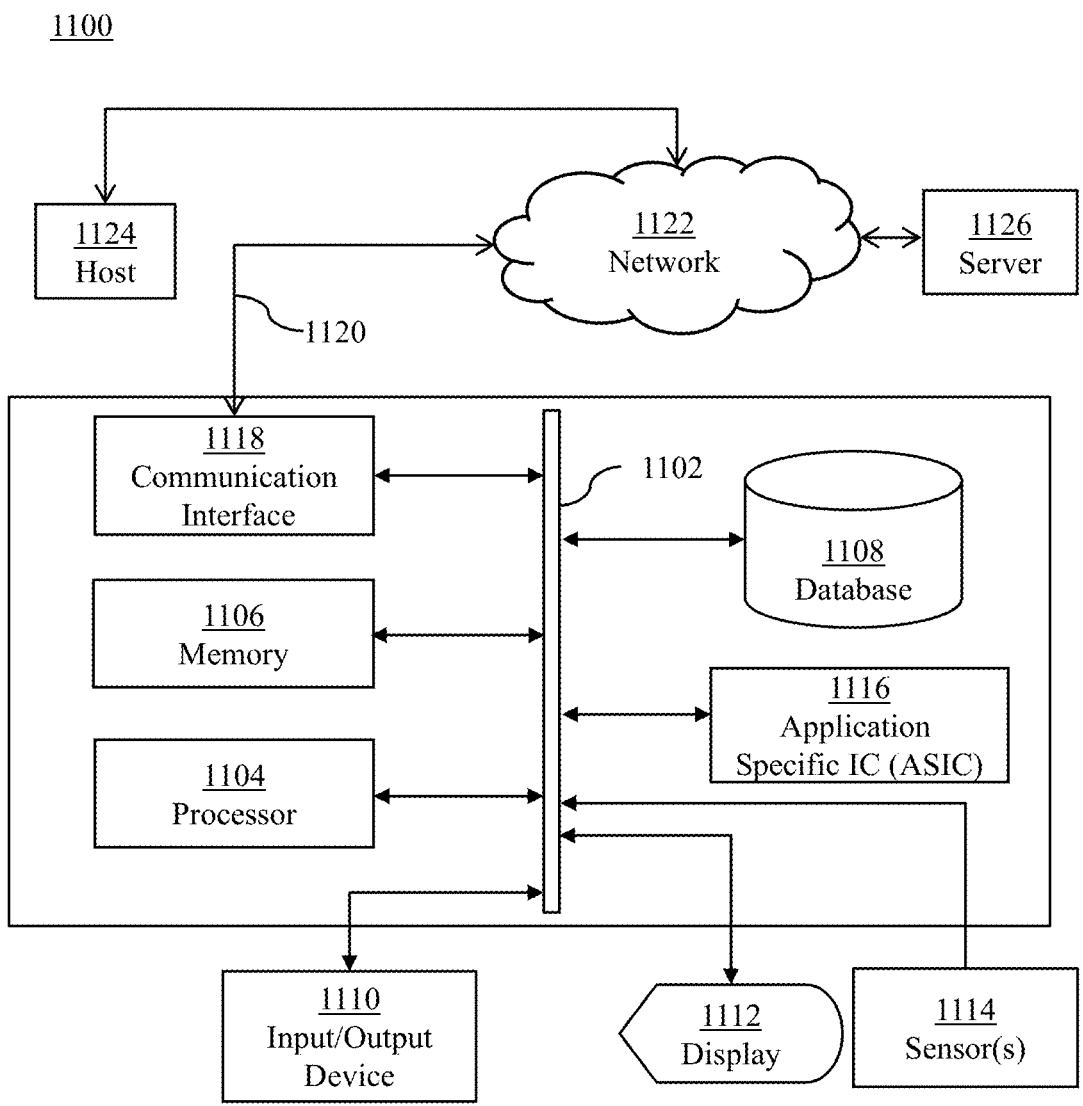
FIG. 11 is a diagram of a computer system that can be used to implement an embodiment of the present invention.

FIG. 11 illustrates a computer system 1100 upon which the operation of the patient device 102, the user device 104, and the health care platform 108 may be implemented. Although, the computer system 1100 is depicted with respect to a particular device or equipment, it is contemplated that other devices or equipment (e.g., network elements, servers, etc.) within FIG. 11 may deploy the illustrated hardware and components of the system. The computer system 1100 is programmed (e.g., via computer program code or instructions) to retrieve data from the health care platform 108 described herein and includes a communication mechanism such as a bus 1102 for passing information between other internal and external components of the computer system 1100. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. The computer system 1100, or a portion thereof, constitutes a means for performing one or more steps for communication medical data.

A bus 1102 includes one or more parallel conductors of information so that information is transferred quickly among devices coupled to the bus 1102. A processor 1104 for processing information are coupled with the bus 1102. The terms processor and controller can be used interchangeably.

The processor 1104 performs a set of operations on information as specified by an end-user. The computer program code is a set of instructions or statements providing instructions for the operation of the processor 1104 and/or the computer system 1100 to perform specified functions.

The code, for example, may be written in a computer programming language that is compiled into a native instruction set of the processor 1104. The code may also be written directly using the native instruction set (e.g., machine language). The set of operations include bringing information in from the bus 1102 and placing information on the bus 1102. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 1104, such as a sequence of operation codes, constitute processor instructions, also called computer system instructions or, simply, computer instructions. The processor 1104 may be implemented as mechanical, electrical, magnetic, optical, chemical, or quantum components, among others, alone or in combination.

The computer system 1100 also includes a memory 1106 coupled to the bus 1102. The memory 1106, such as a Random Access Memory (RAM) or any other dynamic storage device, stores information including processor instructions for storing information and instructions to be executed by the processor 1104. The dynamic memory 1106 allows information stored therein to be changed by the computer system 1100. RAM allows a unit of information stored at a location called a memory address to be stored and retrieved independently of information at neighboring addresses. The memory 1106 is also used by the processor 1104 to store temporary values during execution of processor instructions. The computer system 1100 also includes a Read Only Memory (ROM) or any other static storage device coupled to the bus 1102 for storing static information, including instructions, that is not changed by the computer system 1100. Some memory is composed of volatile storage that loses the information stored thereon when power is lost. Also coupled to the bus 1102 is a non-volatile (persistent) database 1108, such as a magnetic disk, a solid state disk, optical disk or flash card, for storing information, including instructions, that persists even when the computer system 1100 is turned off or otherwise loses power.

Information, including instructions for inspecting the user queries from the medical personnel to the health care platform 108, is provided to the bus 1102 for use by the processor 1104 from an external input device 1110, such as a keyboard containing alphanumeric keys operated by a human user, a microphone, an Infrared (IR) remote control, a joystick, a game pad, a stylus pen, a touch screen, or a sensor. The sensor detects conditions in its vicinity and transforms those detections into physical expression compatible with the measurable phenomenon used to represent information in the computer system 1100. Other external devices coupled to the bus 1102, used primarily for interacting with humans, include a display 1112, such as a Cathode Ray Tube (CRT), a Liquid Crystal Display (LCD), a Light Emitting Diode (LED) display, an organic LED (OLED) display, active matrix display, Electrophoretic Display (EPD), a plasma screen, or a printer for presenting text or images, and a pointing device, such as a mouse, a trackball, cursor direction keys, or a motion sensor, for controlling a position of a small cursor image presented on the display 1112 and issuing commands associated with graphical elements presented on the display 1112, and one or more camera sensors 1114 for capturing, scanning the medical identifiers and/or images, and causing to store one or more still and/or moving images (e.g., videos, movies, etc.). Further, the display 1112 may be a touch enabled display such as capacitive or resistive screen. In some embodiments, for example, in embodiments in which the computer system 1100 performs all functions automatically without human input, one or more of the external input device 1110, and the display 1112 may be omitted.

In the illustrated embodiment, special purpose hardware, such as an ASIC 1116, is coupled to the bus 1102. The special purpose hardware is configured to perform operations not performed by the processor 1104 quickly enough for special purposes. Examples of ASICs include graphics accelerator cards for generating images for the display 1112, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

The computer system 1100 also includes one or more instances of a communication interface 1118 coupled to the bus 1102. The communication interface 1118 provides a one-way or two-way communication coupling to a variety of external devices that operate with their own processors, such as printers, scanners and external disks. In general, the coupling is with a network link 1120 that is connected to a local network 1122 to which a variety of external devices with their own processors are connected. For example, the communication interface 1118 may be a parallel port or a serial port or a Universal Serial Bus (USB) port on a personal computer. In some embodiments, the communication interface 1118 is an Integrated Services Digital Network (ISDN) card, a Digital Subscriber Line (DSL) card, or a telephone modem that provides an information communication connection to a corresponding type of a telephone line. In some embodiments, the communication interface 1118 is a cable modem that converts signals on the bus 1102 into signals for a communication connection over a coaxial cable or into optical signals for a communication connection over a fiber optic cable. As another example, the communication interface 1118 may be a Local Area Network (LAN) card to provide a data communication connection to a compatible LAN, such as Ethernet™ or an Asynchronous Transfer Mode (ATM) network. In one embodiment, wireless links may also be implemented. For wireless links, the communication interface 1118 sends or receives or both sends and receives electrical, acoustic or electromagnetic signals, including infrared and optical signals that carry information streams, such as digital data. For example, in wireless handheld devices, such as mobile telephones like cell phones, the communication interface 1118 includes a radio band electromagnetic transmitter and receiver called a radio transceiver. In certain embodiments, the communication interface 1118 enables connection to the network 110 for inspecting the user queries. Further, the communication interface 1118 can include peripheral interface devices, such as a thunderbolt interface, a Personal Computer Memory Card International Association (PCMCIA) interface, etc. Although a single communication interface 1118 is depicted, multiple communication interfaces can also be employed.

The term "computer-readable medium" as used herein refers to any medium that participates in providing information to the processor 1104, including instructions for execution. Such a medium may take many forms, including, but not limited to, computer-readable storage medium (e.g., non-volatile media, volatile media), and transmission media.

Non-transitory media, such as non-volatile media, include, for example, optical or magnetic disks, such as the database 1108. Volatile media include, for example, the dynamic memory 1106. Transmission media include, for example, twisted pair cables, coaxial cables, copper wire, fiber optic cables, and carrier waves that travel through space without wires or cables, such as acoustic waves, optical or electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a USB flash drive, a Blu-ray disk, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 1116.

The network link 1120 typically provides information communication using transmission media through one or more networks to other devices that use or process the information. For example, the network link 1120 may provide a connection through the local network 1122 to a host computer 1124 or to ISP equipment operated by an Internet Service Provider (ISP).

A server 1126, connected to the Internet, hosts a process that provides a service in response to information received over the Internet. For example, the server 1126 hosts a process that provides information representing video data for presentation at the display 1112. It is contemplated that the components of the computer system 1100 can be deployed in various configurations within other computer systems, e.g., the host 1124 and the server 1126.

At least some embodiments of the invention are related to the use of the computer system 1100 for implementing some or all of the techniques described herein. According to one embodiment of the invention, those techniques are performed by the computer system 1100 in response to the processor 1104 executing one or more sequences of one or more processor instructions contained in the memory 1106. Such instructions, also called computer instructions, software and program code, may be read into the memory 1106 from another computer-readable medium such as the database 1108 or the network link 1120. Execution of the sequences of instructions contained in the memory 1106 causes the processor 1104 to perform one or more of the method steps described herein. In alternative embodiments of the present invention, hardware, such as the ASIC 1116, may be used in place of or in combination with software to implement the invention. Thus, embodiments of the present invention are not limited to any specific combination of hardware and software, unless otherwise explicitly stated herein.

Various forms of computer readable media may be involved in carrying one or more sequence of instructions or data or both to the processor 1104 for execution. For example, instructions and data may initially be carried on a magnetic disk of a remote computer such as the host 1124.

The remote computer loads the instructions and data into its dynamic memory and sends the instructions and data over a telephone line using a modem. A modem local to the computer system 1100 receives the instructions and data on a telephone line and uses an infra-red transmitter to convert the instructions and data to a signal on an infra-red carrier wave serving as the network link 1120. An infrared detector serving as the communication interface 1118 receives the instructions and data carried in the infrared signal and places information representing the instructions and data onto the bus 1102. The bus 1102 carries the information to the memory 1106 from which the processor 1104 retrieves and executes the instructions using some of the data sent with the instructions. The instructions and data received in the memory 1106 may optionally be stored on the database 1108, either before or after execution by the processor 1104.

Additional examples are presented below, by way of example, not limitation.

In a first additional example, an apparatus includes a processor and memory configured to:

output a first set of information associated with a code obtained from a person, wherein the first set of information includes identification information; and output a second set of information associated with the code if biometric data obtained from the person matches biometric data associated with the code.

The processor and memory may be further configured to:

extract at least a portion of the first set of information from the code; and retrieve the second set of information from a remote storage device over a communication network.

The processor and memory may be further configured to extract the biometric data associated with the code from the code.

The processor and memory may be further configured to retrieve the biometric data associated with the code from a remote storage device over a communication network.

The first set of information may include personal identification information.

The second set of information may include personal medical information.

The second set of information may include an indication that the person is a member of an at-risk group.

The second set of information may include an indication that the person is suspected of involvement in illicit activity.

The second set of information may include:

an indication that the person is a member of an at-risk group, an indication that the person is suspected of involvement in illicit activity, or an indication that the person is not member of an at-risk group and is not suspected of involvement in illicit activity.

The processor and memory may be further configured to control a scanner to scan the code from a wristband, a dog tag, a driving license, a car windshield, a financial transaction card, a personal identification card, jewelry, a magnetic device, a mobile phone, a helmet, a label, and/or a wearable article.

The processor and memory may be further configured to control a scanner to scan the code from a passport.

The processor and memory may be further configured to control a scanner to scan the code from an electronic display.

The processor and memory may be further configured to receive the code from an electronic device over a wireless communication channel.

The processor and memory may be further configured to receive the code from a near field communication (NFC) device.

The processor and memory may be further configured to determine that a user is an authorized user prior to outputting the second set of information.

The processor and memory may be further configured to:

validate the person as associated with the code if the biometric data obtained from the person matches the biometric data associated with the code;

invalidate the person if the biometric data obtained from the person does not match the biometric data associated with the code; and output the second set of information if the person is validated.

In a second example, an apparatus includes a processor and memory configured to:

control a scanner to scan a code;

control a biometric sensor to capture biometric data of a person;

compare the biometric data of the person with biometric data associated with the code; and output information associated with the code if the biometric data of the person matches the biometric data associated with the code.

The information may include an indication that the person is a member of an at-risk group.

The information may include an indication that the person is suspected of involvement in illicit activity.

The information may include an:

indication that the person is a member of an at-risk group, an indication that the person is suspected of involvement in illicit activity, or an indication that the person is a not member of an at-risk group and is not suspected of involvement in illicit activity.

One or more of the foregoing examples may be implemented as a method and/or a non-transitory computer readable medium encoded with a computer program that includes instructions to cause a processor to behave accordingly.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

The exemplary embodiments of this present invention have been described in relation to communication devices. However, to avoid unnecessarily obscuring the present invention, the preceding description omits a number of known structures and devices. This omission is not to be construed as a limitation of the scope of the present invention. Specific details are set forth by use of the embodiments to provide an understanding of the present invention. It should however be appreciated that the present invention may be practiced in a variety of ways beyond the specific embodiments set forth herein.

A number of variations and modifications of the present invention can be used. It would be possible to provide for some features of the present invention without providing others.

The present invention, in various embodiments, configurations, and aspects, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the present invention has been presented for purposes of illustration and description. It is not intended to limit the present invention to the form or forms disclosed herein. In the foregoing Detailed Description, for example, various features of the present invention are grouped together in one or more embodiments, configurations, or aspects for the purpose of streamlining the disclosure. The features of the embodiments, configurations, or aspects may be combined in alternate embodiments, configurations, or aspects other than those discussed above. This method of disclosure is not to be interpreted as reflecting an intention the present invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate embodiment of the present invention.

Moreover, though the description of the present invention has included description of one or more embodiments, configurations, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for communicating medical data of at least one individual to at least one user comprising:
    a data collection module configured to collect data, wherein the data comprises identification data and medical data associated with said at least one individual, wherein the identification data comprises at least biometric data, and the medical data comprises a Personal Identifiable Information (MI) data, a Protected Health Information (PHI) data, or a combination thereof;
    a data transformation module configured to encrypt said collected data of said at least one individual;
    at least one Electronic Health Record (EHR) database configured to store said encrypted data of said at least one individual;
    an identifier generation module configured to generate at least one identification code based on said stored encrypted data of said at least one individual, wherein said at least one generated identification code is used for identification of said at least one individual in an offline mode;
a scanning device comprising a scanner configured to scan said generated at least one identification code of said at least one individual and a biometric sensor configured to scan a real-time at least one biometric of said at least one individual;
a validation module configured to validate an identity of said at least one individual, wherein said identity of said at least one individual is validated when said at least one scanned real-time biometric of said at least one individual matches with the at least one of said identification data stored in said at least one of the scanned identification code based on said comparison;
a data access module configured to enable at least one said user to access the medical data of said at least one individual based on a level of authorization for said at least one user defined by said at least one individual in the case in which the identity of said at least one individual has been so validated;
and a user interface module configured to display said accessed medical data on a device of said user,
whereby said code and said biometric data obtained from said individual using said scanning device are used to output a first set of information associated with said code so obtained that includes identification information and a second set of information associated with said code in the case in which said biometric data obtained from said individual matches biometric data associated with said code in the case in which said code has been scanned from one of the group consisting of: a car windshield; jewelry; a magnetic device; a helmet; a label; a wearable; and an electronic display.

2. A machine-implemented method for validating identification data of at least one individual by at least one user, comprising:
    collecting data, wherein said data comprises identification data and medical data associated with said at least one individual, wherein said identification data comprises at least biometric data, and said medical data comprises a Personal Identifiable Information (PII) data, a Protected Health Information (PHI) data, or a combination thereof;
    encrypting said collected data of said at least one individual;
    storing-said encrypted data of said at least one individual in at least one Electronic Health Record (EHR) database;
    generating at least one identification code based on said stored encrypted data of said at least one individual, wherein said at least one generated identification code is used for identification of said at least one individual in an offline mode;
    printing said at least one generated identification code on at least one article;
    scanning, with a scanning device, said printed at least one identification code of said at least one individual, and capturing with a biometric sensor of said scanning device, a real-time at least one biometric of said at least one individual;
    validating an identity of said at least one individual, wherein said identity of said at least one individual is validated when said at least one scanned real-time biometric of said at least one individual matches with said at least one identification data stored in said at least one of said scanned identification codes;

accessing said medical data of said at least one individual based on a level of authorization for at least one user defined by said at least one individual when the identity of said individual has been validated;

displaying said accessed medical data on said user's device;

outputting a first set of information comprising personal identification information of said at least one individual;

comparing said real-time biometric data of said at least one individual with biometric data associated with said code; and outputting a second set of information associated with said code in the case in which said real-time biometric data of the person matches the biometric data associated with said code and said code has been scanned from one of the group consisting of: a car windshield; jewelry; a magnetic device; a helmet; a label; a wearable; and an electronic display.

* * * * *